(12) United States Patent
Glasner et al.

(10) Patent No.: US 11,848,079 B2
(45) Date of Patent: Dec. 19, 2023

(54) BIOMARKER IDENTIFICATION

(71) Applicant: AIC Innovations Group, Inc., New York, NY (US)

(72) Inventors: Daniel Glasner, New York, NY (US); Ryan Scott Bardsley, Manchester, NH (US); Isaac Galatzer-Levy, Brooklyn, NY (US); Muhammad Anzar Abbas, New York, NY (US)

(73) Assignee: AIC Innovations Group, Inc., New York, NY (US)

( * ) Notice: Subject to any disclaimer, the term of this patent is extended or adjusted under 35 U.S.C. 154(b) by 168 days.

(21) Appl. No.: 16/784,132

(22) Filed: Feb. 6, 2020

(65) Prior Publication Data

US 2020/0251190 A1 Aug. 6, 2020

Related U.S. Application Data

(60) Provisional application No. 62/802,049, filed on Feb. 6, 2019.

(51) Int. Cl.
  *G16H 10/20* (2018.01)
  *G16H 50/30* (2018.01)
  (Continued)

(52) U.S. Cl.
  CPC .......... *G16H 10/20* (2018.01); *A61B 5/0022* (2013.01); *A61B 5/165* (2013.01); *A61B 5/4088* (2013.01);
  (Continued)

(58) Field of Classification Search
  None
  See application file for complete search history.

(56) References Cited

U.S. PATENT DOCUMENTS 11,217,033 B1 * 1/2022 Morgan ................ G16H 20/70
2003/0046305 A1 * 3/2003 Clarkson ............... G16H 40/20
(Continued)

FOREIGN PATENT DOCUMENTS

WO WO-2016061320 A2 * 4/2016 ............... A61B 5/16

OTHER PUBLICATIONS

Williamson et al., "Detecting Depression using Vocal, Facial and Semantic Communication Cues," AVEC'16, Oct. 16, 2016, Amsterdam, Netherlands. (Year: 2016).*
(Continued)

*Primary Examiner* — Jonathon A. Szumny
(74) *Attorney, Agent, or Firm* — Fish & Richardson P.C.

(57) ABSTRACT

A method includes: obtaining, by a computer, subject response data including audio data, video data, or audio-video data of a subject's response to one or more stimuli presented to the subject over a defined time period; extracting at least one subject descriptor from the subject response data as a function of time, the at least one subject descriptor including data characterizing involuntary or voluntary action of the subject in response to the one or more stimuli; deriving, from the at least one subject descriptor, a first biomarker characterizing a behavior of the subject in response to the one or more stimuli, in which a value of the first biomarker is indicative of a severity of a disease in the subject; and outputting a disease severity level for the disease as a function of the value of the first biomarker.

26 Claims, 7 Drawing Sheets

(51) Int. Cl.

| | |
|---|---|
| *G16H 50/20* | (2018.01) |
| *G06N 20/00* | (2019.01) |
| *A61B 5/00* | (2006.01) |
| *A61B 5/16* | (2006.01) |
| *G10L 15/08* | (2006.01) |
| *G06V 40/16* | (2022.01) |

(52) U.S. Cl.
CPC .......... *G06N 20/00* (2019.01); *G06V 40/176* (2022.01); *G10L 15/08* (2013.01); *G16H 50/20* (2018.01); *G16H 50/30* (2018.01); *G10L 2015/088* (2013.01)

(56) References Cited

U.S. PATENT DOCUMENTS

| | | | | |
|---|---|---|---|---|
| 2011/0153360 | A1* | 6/2011 | Hanina | G16H 20/60 |
| | | | | 705/3 |
| 2012/0002848 | A1* | 1/2012 | Hill | A61B 5/164 |
| | | | | 382/118 |
| 2012/0183128 | A1* | 7/2012 | Clawson | H04M 3/5116 |
| | | | | 379/45 |
| 2012/0289788 | A1* | 11/2012 | Jain | A61B 5/165 |
| | | | | 702/19 |
| 2012/0316897 | A1* | 12/2012 | Hanina | G16H 20/10 |
| | | | | 705/3 |
| 2013/0266925 | A1* | 10/2013 | Nunamaker, Jr. | G09B 7/00 |
| | | | | 434/362 |
| 2014/0289161 | A1* | 9/2014 | Johnson | G06Q 30/0282 |
| | | | | 705/347 |
| 2014/0313488 | A1* | 10/2014 | Kiderman | A61B 3/113 |
| | | | | 351/246 |
| 2017/0069216 | A1 | 3/2017 | Vaughn et al. | |
| 2017/0262609 | A1* | 9/2017 | Perlroth | G16H 50/30 |
| 2017/0354363 | A1* | 12/2017 | Quatieri | A61B 5/4803 |
| 2017/0365101 | A1* | 12/2017 | Samec | A61B 5/746 |
| 2018/0133507 | A1* | 5/2018 | Malchano | A61N 1/36082 |
| 2018/0184962 | A1* | 7/2018 | Shahaf | G16H 50/20 |
| 2019/0043619 | A1* | 2/2019 | Vaughan | G16H 20/10 |
| 2019/0083031 | A1* | 3/2019 | Hanina | G06T 7/20 |
| 2019/0110754 | A1* | 4/2019 | Rao | G06N 20/00 |
| 2019/0200915 | A1* | 7/2019 | Baker | A61B 5/4088 |
| 2019/0246969 | A1* | 8/2019 | Thomas | A61B 5/7264 |
| 2019/0290127 | A1 | 9/2019 | Hanina et al. | |
| 2019/0290128 | A1 | 9/2019 | Hanina et al. | |
| 2019/0290129 | A1 | 9/2019 | Hanina et al. | |
| 2019/0341152 | A1* | 11/2019 | Mellem | G16H 10/60 |
| 2020/0012897 | A1* | 1/2020 | Sreenivasan | G06N 20/00 |
| 2021/0121125 | A1* | 4/2021 | Tokuno | G16H 50/20 |
| 2021/0358594 | A1* | 11/2021 | Mellem | G16H 10/20 |

OTHER PUBLICATIONS

Gratch et al., "The Distress Analysis Interview Corpus of human and computer interviews," Proceedings of the Ninth International Conference on Language Resources and Evaluation (LREC'14), pp. 3123-3128. (Year: 2014).*
Williamson et al., "Vocal and Facial Biomarkers of Depression Based on Motor Incoordination and Timing," AVEC'14, Nov. 7, 2014, Orlando, FL, USA. (Year: 2014).*
International Search Report and Written Opinion in International Appln. No. PCT/US2020/017081, dated May 11, 2020, 18 pages.
International Preliminary Report on Patentability in International Appln. No. PCT/US2020/017081, dated Aug. 19, 2021, 13 pages.
Alpert, et al., Reflections of depression in acoustic measures of the patient's speech, J Affect Disord. 66(1):59-69 (Sep. 2001).
Amazon Transcribe (https://aws.amazon.com/transcribe/).
Bedi, et al., Automated analysis of free speech predicts psychosis onset in high-risk youths, NPJ Schizophr. 1:15030 (Aug. 2015).
Berenbaum, et al., Emotional experience and expression in schizophrenia and depression J Abnorm Psychol. 101(1):37-44 (Feb. 1992).
Breznitz, Z., Verbal indicators of depression, J Gen Psychol. 119(4):351-63 (Oct. 1992).
Cohn, et al., Detecting depression from facial actions and vocal prosody, 2009 3rd International Conference on Affective Computing and Intelligent Interaction and Workshops (2009) (7 pages).
Cozolino, The oral and written productions of schizophrenic patients, Prog Exp Pers Res. 12:101-52 (1983).
Croisile, et al., Comparative study of oral and written picture description in patients with Alzheimer's disease, Brain Lang. 53(1):1-19 (Apr. 1996).
Delisi, Speech disorder in schizophrenia: review of the literature and exploration of its relation to the uniquely human capacity for language, Schizophr Bull. 27(3):481-96 (2001).
Ekman, et al., Autonomic nervous system activity distinguishes among emotions, Science. 221(4616):1208-10 (Sep. 1983).
Ekman, et al., What the Face Reveals: Basic and Applied Studies of Spontaneous Expression Using the Facial Action Coding System (FACS), Oxford University Press, New York (1997) (662 pages).
Gao, et al., Model-based and Model-free Machine Learning Techniques for Diagnostic Prediction and Classification of Clinical Outcomes in Parkinson's Disease Sci Rep. 8(1):7129 (May 2018).
Gottheil, et al., Appropriate and Background Affect in Facial Displays of Emotion Comparison of Normal and Schizophrenic Males, Arch Gen Psychiatry. 33(5):565-8 (May 1976).
Guinn, et al., Language analysis of speakers with dementia of the Alzheimer's type, 2012 AAAI Fall Symposium Series (2012) (6 pages).
Harel, et al., Variability in fundamental frequency during speech in prodromal and incipient Parkinson's disease: A longitudinal case study, Brain Cogn. 56(1):24-9 (Oct. 2004).
Harrigan, et al., How do you look when feeling anxious? Facial displays of anxiety, Personality and Individual Differences 21(2):205-212 (Aug. 1996).
Ho, et al., Speech volume regulation in Parkinson's disease: effects of implicit cues and explicit instructions, Neuropsychologia. 37(13):1453-60 (Dec. 1999).
Jarrold, et al., Aided diagnosis of dementia type through computer-based analysis of spontaneous speech. Proceedings of the Workshop on Computational Linguistics and Clinical Psychology: From Linguistic Signal to Clinical Reality (Jun. 2014) (11 pages).
Katsikitis, et al., A study of facial expression in Parkinson's disease using a novel microcomputer-based method, J Neurol Neurosurg Psychiatry. 51(3):362-6 (Mar. 1988).
Kliper, et al., Prosodic analysis of speech and the underlying mental state, International Symposium on Pervasive Computing Paradigms for Mental Health (2015).
Little, et al., Suitability of dysphonia measurements for telemonitoring of Parkinson's disease, Nature Precedings (Sep. 2008) (27 pages).
Logmmse (https://pypi.org/project/logmmse/).
Michaelis, et al., Glottal-to-Noise Excitation Ratio—a New Measure for Describing Pathological Voices, Acustica 83:700-706 (1997).
OpenFace: Overview (https://cmusatyalab.github.io/openface) (5 pages) (2016).
Ozdas, et al., Investigation of vocal jitter and glottal flow spectrum as possible cues for depression and near-term suicidal risk, IEEE Trans Biomed Eng. 51(9):1530-40 (Sep. 2004).
Parselmouth/Pratt (https://github.com/YannickJadoul/Parselmouth; https://www.ee.iitb.ac.in/student/~daplab/resources/SpeechAnalysisUsingPRAAT.pdf (13 pages) (May 2019).
Rapcan, et al., Acoustic and temporal analysis of speech: A potential biomarker for schizophrenia. Med Eng Phys. 32(9):1074-9 (Nov. 2010).
Rude, et al., Self-report and cognitive processing measures of depressive thinking predict subsequent major depressive disorder, Cognitive Therapy and Research 34(2):107-115 (Apr. 2010).
Saxman, et al., Speaking fundamental frequency and rate characteristics of adult female schizophrenics, J Speech Hear Res. 11(1):194-203 (Mar. 1968).
Siderowf et al., Test-retest reliability of the unified Parkinson's disease rating scale in patients with early Parkinson's disease: results from a multicenter clinical trial, Mov Disord. 17(4):758-63 (Jul. 2002).

(56) References Cited

OTHER PUBLICATIONS

Skodda, et al., Speech rate and rhythm in Parkinson's disease, Mov Disord. 15;23(7):985-992 (May 2008).

Stacy, et al., Development of a Patient Questionnaire to facilitate recognition of motor and non-motor wearing-off in Parkinson's disease, Journal of Neural Transmission, 114(2):211-7 (Mar. 2007).

Trifu, et al., Linguistic Indicators of Language in Major Depressive Disorder (MDD). An Evidence Based Research, Journal of Evidence-Based Psychotherapies 17(1):105-128 (Mar. 2017).

Zhang, et al., Energy distribution analysis and nonlinear dynamical analysis of phonation in patients with Parkinson's disease, 2017 Asia-Pacific Signal and Information Processing Association Annual Summit and Conference (APSIPA ASC), Kuala Lumpur, pp. 630-635 (2017).

\* cited by examiner

BIOMARKER IDENTIFICATION

CROSS-REFERENCE TO RELATED APPLICATIONS

This application claims priority to U.S. Provisional Patent Application Ser. No. 62/802,049, filed on Feb. 6, 2019, the contents of which are incorporated here by reference in their entirety.

BACKGROUND

Disease diagnosis and monitoring is an ongoing challenge across multiple fields of medicine. Automated tools have the potential to enable widely-available and reliable determination of disease severity.

SUMMARY

The present disclosure relates to biomarker identification and determination of disease severity.

A method includes: obtaining, by a computer, subject response data including audio data, video data, or audio-video data of a subject's response to one or more stimuli presented to the subject over a defined time period; extracting at least one subject descriptor from the subject response data as a function of time, the at least one subject descriptor including data characterizing involuntary or voluntary action of the subject in response to the one or more stimuli; deriving, from the at least one subject descriptor, a first biomarker characterizing a behavior of the subject in response to the one or more stimuli, in which a value of the first biomarker is indicative of a severity of a disease in the subject; and outputting a disease severity level for the disease as a function of the value of the first biomarker.

In some implementations, the method includes obtaining, by the computer, a selection by the subject of a presented answer choice in response to a directed question, and the disease severity level is based on the first biomarker and the selection.

In some implementations, the one or more stimuli include a first stimulus and a second stimulus, and the defined time period includes a first period of time during which the subject is responding to the first stimulus and a second period of time during which the subject is responding to the second stimulus, and the method includes deriving a second biomarker based on at least one extracted subject descriptor from the first period of time; and deriving a third biomarker based on at least one extracted subject descriptor from the second period of time, in which the disease severity level is based on the first biomarker, the second biomarker, and the third biomarker. In some implementations, the first stimulus is a display of a positively valenced image, and the second stimulus is a display of a negatively valenced image. The first stimulus is a positively valenced question, and the second stimulus is a negatively valenced question. The first stimulus and the second stimulus are two different types selected from the following stimulus types: a request to make a face having a specified emotion, a request to make a specified sound, and an open-ended question In some implementations, the at least one subject descriptor includes data characterizing a facial movement of the subject. The at least one subject descriptor includes data characterizing a verbal acoustic characteristic of the subject. The at least one subject descriptor includes applying a machine learning process to the subject response data. Extracting the subject descriptors includes applying a signal decomposition process to the subject response data.

In some implementations, the method includes deriving, from the at least one subject descriptor, a second biomarker and a third biomarker, in which the disease severity level is based on the first biomarker, the second biomarker, and the third biomarker. The second biomarker and the third biomarker are two different types selected from the following biomarker types biomarker: facial behavior, verbal, and speech. The first biomarker characterizes an emotional facial expressivity of the subject. Deriving the first biomarker includes: extracting transcribed speech from the subject response data, the transcribed speech including transcribed words; based on at least a portion of the transcribed words, determining one or more speech descriptors; and deriving, from the at least a portion of the transcribed words, a second biomarker characterizing a speech behavior of the subject in response to the one or more stimuli, in which the disease severity level is based on the first biomarker and the second biomarker.

In some implementations, the method includes: based on the first biomarker, sending, to a controller controlling a display unit, instructions to present a particular stimulus to the subject using the display unit. The one or more stimuli include an instruction to the subject to take a medication, and the subject response data includes video data showing the subject taking the medication. The one or more stimuli are presented to the subject by a display of a device, a processor of the device controls the display, and a camera of the device records the subject response data. The method includes receiving stimulus data, the stimulus data including respective types of the one or more stimuli, and time portions, of the defined time period, corresponding to subject response to each of the one or more stimuli, and the at least one subject descriptor is extracted based on the respective types of the one or more stimuli. The method includes: based on subject data indicating a potential disease exhibited by the subject, sending, to a controller controlling a display unit, instructions to present a particular stimulus to the subject using the display unit.

A system includes: a display; a controller, the controller configured to send instructions to the display to present one or more stimuli to a subject over a defined time period; a sensor configured to record subject response data including audio data, video data, or audio-video data of the subject's response to the one or more stimuli; and a computer, the computer configured to perform operations including: obtaining the subject response data; extracting at least one subject descriptor from the subject response data as a function of time, in which the at least one subject descriptor includes data characterizing involuntary or voluntary action of the subject in response to the one or more stimuli; deriving, from the at least one subject descriptor, a first biomarker characterizing a behavior of the subject in response to the one or more stimuli, in which a value of the first biomarker is indicative of a severity of a disease in the subject; and outputting a disease severity level for the disease as a function of the value of the first biomarker.

In some implementations, the operations include: based on the first biomarker, sending an instruction to the controller to have the display present a particular stimulus to the subject. The display, the controller, and the sensor are integrated into a portable device. The operations include: obtaining a selection by the subject of a presented answer choice in response to a directed question, in which the disease severity level is based on the first biomarker and the selection.

In some implementations, the one or more stimuli include a first stimulus and a second stimulus, and the defined time period includes a first period of time during which the subject is responding to the first stimulus and a second period of time during which the subject is responding to the second stimulus, and the operations include: deriving a second biomarker based on at least one extracted subject descriptor from the first period of time; and deriving a third biomarker based on at least one extracted subject descriptor from the second period of time, the disease severity level being based on the first biomarker, the second biomarker, and the third biomarker. The first stimulus and the second stimulus are two different types selected from the following stimulus types: a request to make a face having a specified emotion, a request to make a specified sound, and an open-ended question. The operations include: receiving, from the controller, stimulus data, the stimulus data including respective types of the one or more stimuli, and time portions, of the defined time period, corresponding to subject response to each of the one or more stimuli, in which the at least one subject descriptor is extracted based on the respective types of the one or more stimuli.

In some implementations, deriving the first biomarker includes: extracting transcribed speech from the subject response data, the transcribed speech including transcribed words; based on at least a portion of the transcribed words, determining one or more speech descriptors; and deriving, from the at least a portion of the transcribed words, a second biomarker characterizing a speech behavior of the subject in response to the one or more stimuli, in which the disease severity level is based on the first biomarker and the second biomarker. The operations include based on subject data indicating a potential disease exhibited by the subject, sending, to the controller, instructions to present a particular stimulus to the subject using the display.

Particular embodiments of the subject matter described in this specification can be implemented to realize one or more of the following advantages. Multiple forms of a subject's response can be collected in response to varied stimuli. Response to a single stimulus may be analyzed to derive multiple biomarkers or multiple types of biomarkers. Subject response data can be collected in sessions of short duration occurring at higher frequency than is typical for human-administered tests. Sessions can be structured to lead to repeatable, stable, and useful subject response output. Computationally extracted subject response descriptors can indicate features unquantifiable by human observation alone. Biomarkers can be more accurate and more stable than typical doctor-administered scales. Multiple types of biomarkers can be analyzed simultaneously to give more accurate and reliable determination of disease severity. Computationally derived biomarkers can be combined with subjects' selection of presented answer choices to give more accurate and reliable disease determination of disease severity. Computational derivation of biomarkers can enable measurements of large populations. Biomarkers can be derived based on the particular stimulus giving rise to subject response. Stimuli can be presented based on a biomarker that would be useful to derive based on a possible disease that the subject may have. Stimuli can be presented in order to generate useful subject response data.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more implementations are set forth in the accompanying drawings and the description below. Other features and advantages will be apparent from the description and drawings, and from the claims.

DETAILED DESCRIPTION

Figure 1:
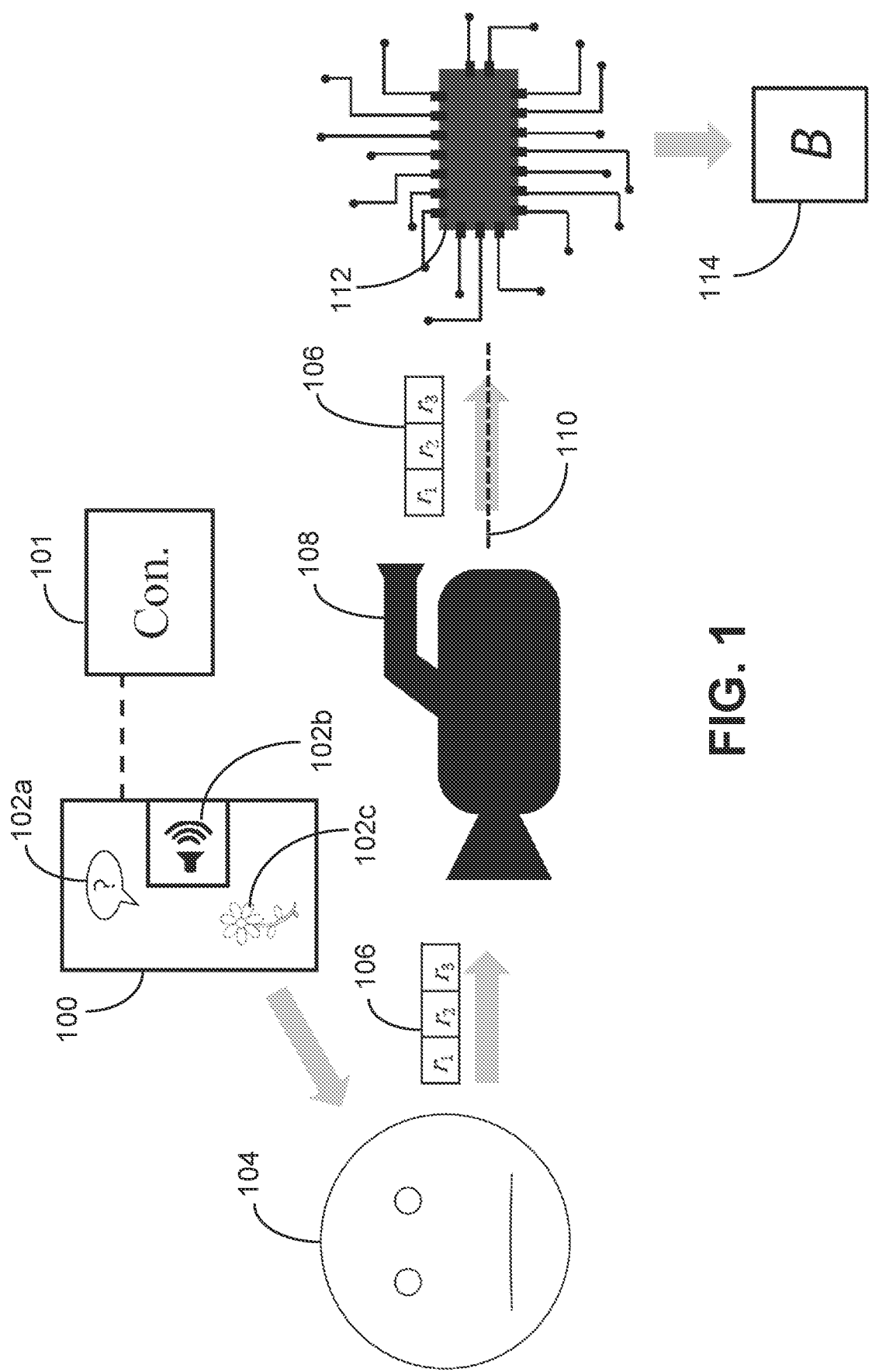
FIG. 1 is a block diagram of exemplary subject response data collection and processing

The present disclosure relates to biomarker identification and determination of disease severity. In particular, this disclosure relates to deriving disease biomarkers based on subject response data.

When diagnosing a disease or condition in a subject, doctors often quantify the behavior of the subject according to a pre-existing scale. Inputs to such scales may be, for example, the subject's verbal responses to questioning, observations of the subject made by the subject's family, and/or observations by a doctor of the subject's movement. These and other measures are combined into a number that, when interpreted according to the scale's prescription, indicate a presence, severity, or progression of the disease.

However, these traditional scales present possible problems. For example, scale inputs may be subjective, such that the same subject may be scored differently by different doctors or by the same doctor at different times. This may cast doubt on the reliability of doctor-administered scales, even well-attested ones, for characterizing disease.

In addition, many existing scales depend on lengthy question-and-answer sessions between doctor and subject. During the course of these sessions, which may last an hour or more, the present state of the subject may itself change, invalidating the assumptions of the scale. And the length of these sessions means that frequent repetition of testing—for example, daily testing—may be time- or cost-prohibitive. That is, existing scale-based methods make it difficult to acquire many data points for the same person, since each data point is obtained via medical examination by a qualified tester.

In previous disclosure United States Patent Application Publication 2019/0290127 A1, incorporated herein by reference, it was described how short-time-scale responses to stimuli can indicate subject states. For example, subconscious facial movements of a subject in the first 250 milliseconds after being shown a stimulus, before thoughtful action takes over, can be useful for diagnostic purposes.

This disclosure will describe how the short-time-scale responses, as described in US 2019/0290127 A1, and other subject responses may be used in the derivation of digital biomarkers indicative of disease.

Biomarkers are quantifiable characteristics of health. They are used to identify disease states and assess treatment response. Digital biomarkers are digitally-based measures of biomarkers whose derivation can be automated for remote assessment via technologies such as smartphones, wearables, and sensors. By doing so, disease identification and assessment of disease severity can become more sensitive, objective, and scalable. Biomarkers may also indicate a subject's response to a medication regimen.

The subject matter of the present disclosure includes, among other things, recording, storing, and processing both video and audio of subject behavior in order to derive both visual and auditory biomarkers of disease and subject state. This may include capturing facial expressivity, verbal acoustics, content of speech, and patterns of movement. The subject data may be a response to presented stimuli.

FIG. 1 shows a process for obtaining and processing subject response data. First, a display 100, controlled by a controller 101, presents stimuli 102a, 102b, 102c to a subject 104. The subject 104 reacts, and the resulting subject response data 106 is captured by a capture device 108. The capture device 108 then transmits the subject response data 106 over a path 110 to a computational analysis unit 112. The computational analysis unit 112 process the subject response data 106 and outputs a biomarker 114.

In some implementations, the display 100 is a mobile phone display, the associated mobile phone having installed an application for administering the stimuli. In some implementations, the display 100 is, for example, a laptop display, a computer monitor, or a television display. In some implementations, the display 100 has an integrated speaker for output of audio. In some implementations, the display 100 includes, or is connected to, a user interface device, e.g., a touchscreen or keyboard. The controller 101 may be, for example, a mobile phone processor or a computer processor.

The stimuli 102a-102c may take a variety of forms, as will be described below. The stimuli may include, for example, questions for the subject to answer, in which the questions are administered by displaying text or by outputting audio or by both. The stimuli may include pictures or video or both. The stimuli may include instructions of actions for the subject 104 to perform.

As will be described in more detail below, the subject response data may take a variety of forms. In some implementations, the capture device 108 captures still images, video images and/or audio. In some implementations, the capture device 108 captures textual input from the subject 104. In some implementations, the capture device 108 captures selections by the subject 104.

The capture device 108 may be integrated into the display 100. For example, in some implementations, the capture device 108 is a mobile phone camera. In such cases, the mobile phone may display the stimuli 102a-102c via the display 100, and capture, by the camera, the response of the subject 104, for example, in the form of audiovisual data. In some implementations, the capture device 108 is separate from the display 100. The capture device 108 may include sensors, e.g., microphones and accelerometers.

The computational analysis unit 112 may be integrated into the display 100 and/or the capture device 108. For example, in some implementations, the computational analysis unit 112 (e.g., a computer) includes a processor and memory inside the same mobile phone as the display 100 and the capture device 108, and the transmission path 110 is an intra-phone data transfer. In some implementations, the computational analysis unit 112 includes at least one server remote from the capture device 108, and the transmission path 110 is, for example, a wireless transmission path and/or wired transmission path. The transmission path may include a path over a local area network or a wide area network including, e.g., an Internet-based transmission path. In some implementations, the computational analysis unit 112 is the same as or includes the controller 101. In some implementations, the computational analysis unit 112 is communicably connected to the controller 101 using a transmission path such as transmission path 110. In some implementations, the computational analysis unit 112 is implemented as a cloud-based remote server.

Implementations in which the display 100, the controller 101, and the capture device 108 are integrated together, and in which the computational analysis unit 112 is either integrated with the those units or readily communicable with them, provide several advantages. For example, a subject downloads a "Parkinson's Testing Application" to their smartphone. The executable application, via the controller 101 and the display 100, displays stimuli to which the subject responds, with the subject response data captured by the phone's front-facing camera. Processing and analysis are either performed by the phone itself or by one or more backend servers that can quickly calculate and analyze biomarkers and transmit the results back to the phone or to other computing devices. Not only does the subject have easy access to their test results, but the test can also be performed often—even multiple times a day—without requiring a visit to a doctor's office and without incurring significant cost. The app can display notifications to the subject when the subject is due for each testing session.

Figure 2:
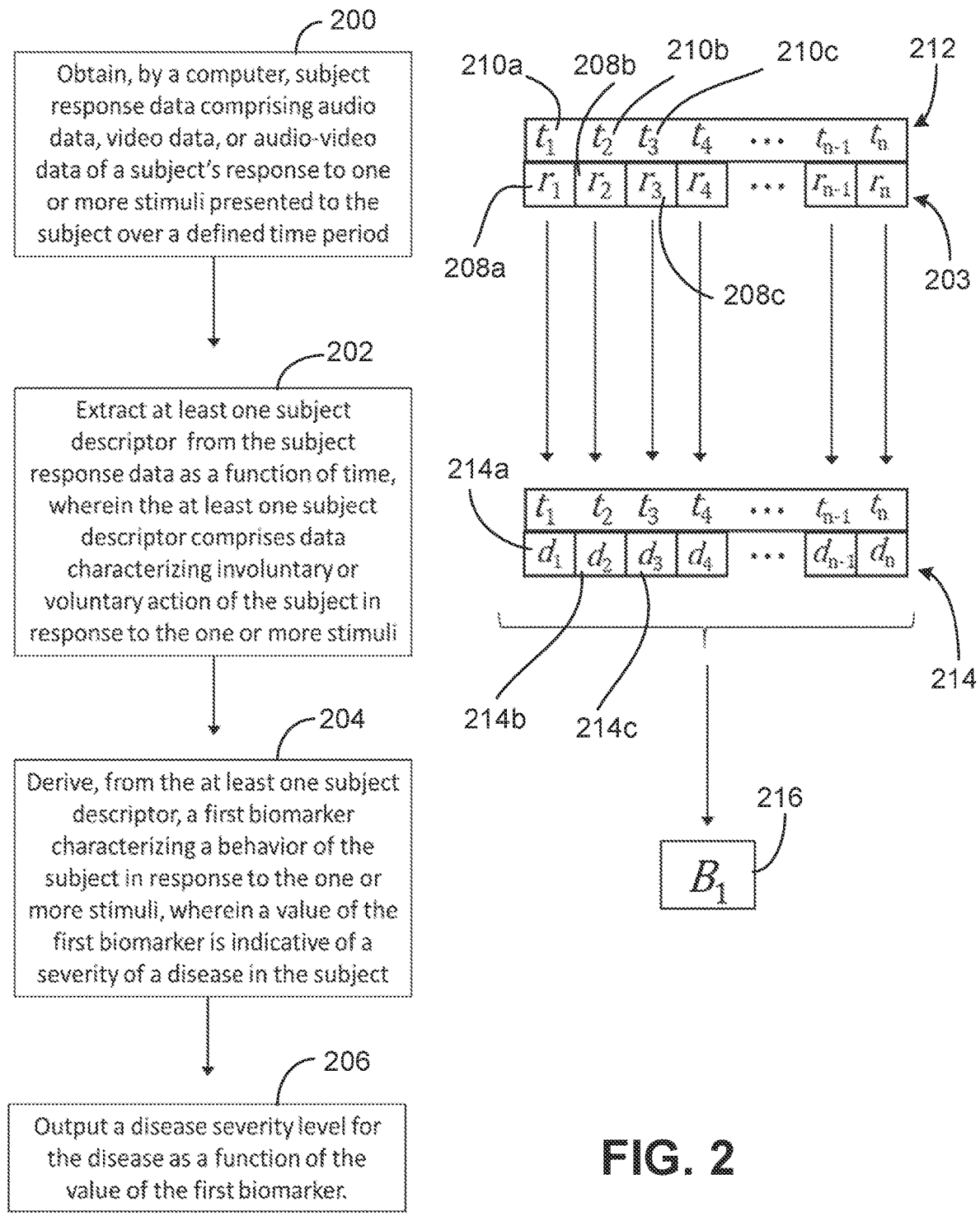
FIG. 2 is a flow chart and block diagram of exemplary subject response data processing

FIG. 2 shows a process for deriving biomarkers from obtained subject response data. The process covered by steps 200, 202, 204, 206 may be performed by a computational analysis unit, such as computational analysis unit 112. In step 200, the computational analysis unit obtains subject response data 208 (e.g., units of subject response data $r_i$, e.g., 208a, 208b, 208c) for each time point (e.g., time points $t_i$ in FIG. 2, e.g., 210a, 210b, 210c) of a set of time points 212 in a defined time period, in which the subject response data has been collected in response to one or more stimuli presented to a subject.

Each unit of subject response data 208 may be, for example, a frame of video recorded of the subject. For example, a display, such as the display 100, might output an image of a country meadow and ask the subject to respond to the image over the course of 10 seconds. If a capture device, such as the capture device 108, is a video recorder capturing video at 60 frames per second, then 600 units of subject response data, corresponding to 600 time points and to 600 frames of video, are recorded and obtained by the computational analysis unit. In some implementations, subject response may be recorded over a longer or shorter period of time than 10 seconds, or the subject response time may be determined by the subject's response itself.

In some implementations, the subject response data is audio data, and each unit of subject response data is a frame of audio data. In some implementations, video and audio data are combined, such that each unit of subject response data is a frame of combined video and audio data.

In step 202 of FIG. 2, the computational analysis unit extracts, for each time point $t_i$, one or more subject descriptors $d_i$ 214 (e.g., 214a, 214b, 214c) from the subject response data of the corresponding time point. A subject descriptor may characterize involuntary or voluntary action of the subject in response to the one or more stimuli. One or more subject descriptors may be extracted as a function of time.

In step 204, a first biomarker 216 is derived based on the extracted subject descriptors $d_i$. The first biomarker characterizes a behavior of the subject in response to the one or more stimuli, and a value of the first biomarker is indicative of a severity of a disease in the subject.

In step 206, the computational analysis unit outputs a disease severity level for the disease as a function of the value of the first biomarker. The disease severity level may be, for example, a binary indicator of whether or not the subject has the disease. The disease severity level may be an indicator of a degree of the disease, a progression of the disease, and/or a response by the disease to a treatment.

For example, referring to FIG. 2, the subject response data may be an audio recording including audio frames ($r_1$, $r_2$, ... $r_n$). The recording, in step 202, is processed in order to obtain subject descriptors in the form of a frame-wise sound intensity vector ($d_1$, $d_2$, ... $d_n$). In step 204, the average sound intensity over the time period $t_1$-$t_n$ is derived, and/or, for example, a sequence of sound intensities is derived. The average sound intensity is a biomarker that may be used as an indicator of the presence and/or severity of a disease in the subject.

Although FIG. 2 shows a single type of subject descriptor 216, in some implementations multiple subject descriptors are extracted from each frame. For example, besides frame-wise sound intensity, step 202 might also include extracting frame-wise harmonics data. For example, a fundamental frequency of the audio data of each frame and/or harmonic frequencies of the audio data of each frame may be extracted.

Furthermore, in some implementations, further intermediate processing steps are performed before derivation of the biomarker. In one example, a frame of video (analogous to 208a) is analyzed for facial muscle position (analogous to 214a). Then, each frame's facial muscle positioning is analyzed to determine, on a frame-wise basis, or on a basis of sequences of frames, the strength of an exhibited emotion; this is another subject descriptor. Finally, one or more biomarkers (analogous to 216) are derived based on the frame-wise emotion strength data.

In some implementations, extracted subject descriptors do not share a one-to-one relationship with the subject response data from which they are derived. For example, if a tremor-related biomarker requires the derivation of frame-to-frame movement, then an intermediate subject descriptor might measure frame-to-frame movement of the subject. It may not be possible to calculate this movement-related subject descriptor for every single frame of subject response data. Data from multiple adjacent units of subject response data may be combined and analyzed to produce subject descriptors, such that, for example, there is 1 unit of subject descriptor data for every 3 units of subject response data.

The biomarker 216 may be used as indicators of a presence and/or severity of a disease in the subject. Alternatively, or in addition, the biomarker may be used as indicators of a subject's response to treatment over a period of time.

The biomarker 216 is a combined value that aggregates information contained in the time-point-wise subject response data 214. For example, the derived biomarker 216 might be an average value of the $r_i$, a sum of the $r_i$, etc. Further examples of implemented biomarkers are given below.

In some implementations, the biomarker is a sequence of values, e.g., the biomarker 214 might be a particular sequence of the ($r_i$, $r_{i+1}$, ... $r_{i+m}$) as shown in FIG. 2.

In some implementations, the subject response data is "raw" data, that is, unprocessed audiovisual data. In some implementations, the subject response data is filtered and/or noise-reduced before step 202 of FIG. 2.

In some implementations, the subject response data is recorded while the subject ingests a medication. The stimulus might be an instruction to the subject to take the medication, and the corresponding subject response data might be video data showing the subject taking the medication. This subject response data, which can be referred to as "dosing subject response data," may act as proof that the medication was taken. In some implementations, the dosing subject response data may be further analyzed to derive biomarkers, as described herein.

The extraction of the subject descriptors and the derivation of biomarkers is performed computationally by a computer. For example, the extraction or derivation of a biomarker might include one or more of a machine learning step, a signal decomposition step, an audio processing step, or an image processing step performed by a specially programmed computer. For example, while a doctor may be able to subjectively observe, to some extent, whether a subject is "sad" or "happy," the doctor would not be able to (in one example of processes described herein) extract a fundamental harmonic frequency from each moment of the subject's voice and perform derivations based on those frequencies, nor would the doctor be able to analyze miniscule facial movements and apply a deep learning algorithm to those movements in order to measure "sadness" or "happiness" using an objective, repeatable metric.

In some implementations, the computational analysis unit obtains, in addition to subject response data, stimulus data indicating the one or more stimuli presented to the subject. The stimulus data may be referenced to the subject response data, such that the computational analysis unit may determine, for each unit of subject response data, what particular stimulus the subject was responding to.

In some implementations, when the computational analysis unit obtains both the subject response data and the stimulus data, the computational analysis unit may derive biomarkers, and perform the other steps of FIG. 2, based on each stimulus. For example, certain subject descriptors and associated biomarkers may be more indicative of disease severity when the associated subject data was produced in response to a first set of one or more stimuli than when the associated subject was produced in response to a second set of one or more stimuli. A speech biomarker, for example, may be a reliable indicator of disease severity when the subject was responding to a subject interview stimulus (see below), and the same speech biomarker may be a less reliable indicator of disease severity when the subject was responding to valenced image presentation stimulus. Therefore, more instructive biomarkers may be obtained than if the computational analysis unit does not receive stimulus data.

In implementations where the computational analysis unit obtains information about the stimuli associated with the subject response data, the computational analysis unit may tailor the computational analysis unit's analysis to the biomarkers that might be most indicative of disease severity. This may improve device efficiency by allowing fewer calculations to be performed.

Figure 3:
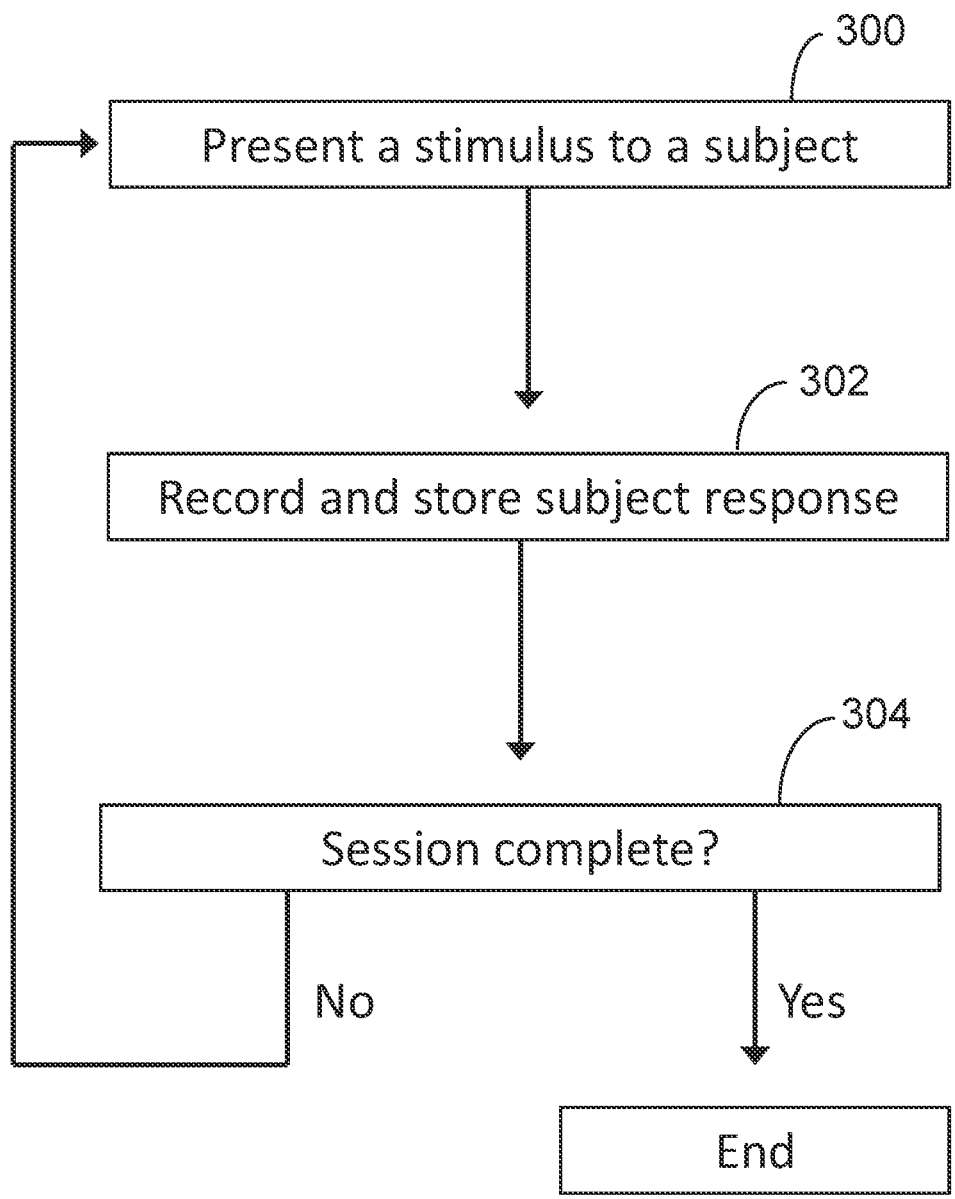
FIG. 3 is a flow chart of an exemplary response collection session

In some implementations, subject response data is collected during discrete sessions taking the form of automated interviews. FIG. 3 shows a flowchart of a session process. In step 300, a stimulus is presented to a subject. The subject reacts, and the response is stored as subject response data in step 302. In step 304, if the session is complete, the process ends; if not, a further stimulus is provided.

In some implementations, the subject response itself dictates whether there will be a further stimulus in the session, and/or the subject response dictates what the further stimulus will be. For example, if the subject does not speak for long enough in responding to a stimulus, the session may be automatically altered to output the stimulus "please continue speaking" (e.g., through audio, video, and/or displayed text) and additional time may be allocated for recording of the subject response.

In some implementations, the presented stimuli are determined based on branching logic. The branching logic applies a real time analysis of subject responses as well as an analysis of the context of the subject responses to provide more efficient and accurate monitoring. Branching not only considers the answers provided, but also context such as, for example, the amount of time to respond, any delays in speech, the inflection of the voice of the subject, measurements of levels of excitement or lack thereof, or any other number of non-traditional branching logic indicators, thus allowing for branching of presented stimuli in response to a holistic view of the user, rather than simply their response to the prior stimulus.

This flexibility allows for the session to be conducted in a more conversational manner, keeping the subject more comfortable while maximizing the amount of relevant information extracted from the interview systems. Additionally, such an automated system removes bias that may be introduced by a human interviewer, or because of inter-interviewer and intra-interviewer differences in presentation or evaluation criteria. Accordingly, the presently disclosed unique systems provide objective and repeatable benefits.

In some implementations, the computational analysis unit quickly analyzes obtained subject response data and, based on the subject response data and/or biomarkers obtained from the subject response data, selects stimuli to be presented to the user in the current session. For example, if a subject's derived verbal biomarkers in response to a first stimulus indicate that the subject may be suffering from depression, an additional stimulus may be added, in real time, to the current session, the additional stimulus leading to a response that can be analyzed for further evidence of depression.

In some implementations, this is accomplished by the computational analysis unit 112 sending an instruction to the controller 101 that controls a display presenting the stimuli, the instruction indicating the additional stimulus to be presented. In some implementations, the computational analysis unit 112 sends instructions to the controller 101 to determine stimuli for a future session.

In another example, if the subject displays a strong negative emotional reaction to a particular stimulus, the computational analysis unit 112 may send an instruction to the controller 101 to terminate the session.

Stimuli may take any one of at least several forms. In some implementations, stimuli engage subjects in active verbal and visual interactions with a smartphone application. The stimuli assist in optimizing subject behavior for the collection of informative subject response data.

The following types of stimulus may be presented to the subject, and the responses analyzed (e.g., for derivation of biomarkers), using the system of FIG. 1. The stimuli may presented be via the display 100, the display 100 including, in some implementations, a speaker. The type of stimulus presented, or the specific stimulus presented, might by selected by the controller 101 or by the computational analysis unit 112 communicably coupled to the controller 101. The type of stimulus presented, or the specific stimulus presented, might depend on, for example, a specific disease to be detected, a history or a preference of the subject, and other parameters. These parameters may be processed by the controller 101 and/or the computational analysis unit 112 in order to indicate at least a type of stimulus presented, the specific stimulus presented, a number of stimuli presented, and a schedule of sessions of stimuli to be presented. The computational analysis unit 112 may derive biomarkers from the subject response data.

In some implementations, the following types of stimulus might be combined into a single stimulus. That is, a given stimulus may not be defined neatly according to these categories.

Some stimuli include subject interviews about their general well-being in the hours surrounding the session. This includes activities they have been participating in, activities they plan on participating in, and the level of enjoyment associated with those activities. Biomarkers on facial and verbal expressivity, content of speech, and overall movement are derived. The task is designed to be short so that it may be deployed at high frequencies. As a result, the subject interview can be scheduled multiple times in one day and several times a week. A subject interview might take approximately 1 minute to complete.

Some stimuli include presenting the subject with a safe subset of positively, neutrally, and negatively valenced images from an image dataset, e.g., the Open Affective Standard Image Set (OASIS). OASIS is an open-access image set containing 900 images depicting a broad spectrum of themes whose valence has been rated by over 800 people. For example, the stimuli might include 3 positively valenced images and 3 negatively valenced images padded with 7 neutrally valenced images. Subjects responding to the images are asked to verbally describe each of the images and the emotions they trigger. Biomarkers of facial and verbal expressivity, content of speech, and movement are derived. Image presentation might take approximately 4 minutes to complete.

Some stimuli include asking the subject to express and hold six basic facial expressions: happiness, sadness, anger, disgust, surprise, and fear. The subject is also asked to make the most expressive face they can. Biomarkers on facial expressivity and movement are derived and are used to measure both the ability to express and hold certain emotions and the extent to which they are expressed. A facial expression task might take approximately 1 minute to complete.

Some stimuli include asking the subject to pronounce sustained vowel sounds and recite the names of the days of the week. Sustained vowel sounds allow collection of verbal behavior that can be analyzed for vocal tremors. Recitation of the days of the week allows collection of a speech sample that can be used to train natural language processing models, which are used to calculate speech biomarkers across stimuli that may be involved in a session or sequence of sessions. Requested sound tasks might take approximately 1 minute to complete.

An example session is shown in Table 1. In this case, the subject would open an app on their smartphone and be shown stimuli, such as the "prompts" listed in Table 1. The smartphone includes the display 100 the controller 101, and the capture device 108 (for example, a front-facing smartphone camera) of FIG. 1. In some implementations, biomarker derivation is performed on the smartphone itself, such that the computational analysis unit 112 is, for example, a processor and memory of the smartphone. In some implementations, biomarker derivation is performed on one or more remote servers, and subject response data may be sent from the smartphone to the one or more remote servers using, for example, a wireless network, a near-field communication device.

Image, audio, and/or video data of the subject may be recorded as the subject reacts to the responses. Completion of the session enables the derivation of biomarkers indicative of the presence of schizophrenia.

Because the stimuli in a given session can be presented in a pre-determined manner, and because responses to the stimuli can be computationally analyzed in an objective manner, the biomarkers disclosed herein are, in some implementations, more reliable than those determined by doctors in typical practice.

In some implementations, stimuli include directed questions to which the subject responds by selecting one of two or more presented answer choices. For example, a stimulus might be the spoken or displayed directed question "Have you had a good week?", and a corresponding answer might be given by the user selecting "Yes" or "No" by clicking a corresponding displayed button. In some implementations,

TABLE 1

Session for detection of Schizophrenia

| Displayed Text | Description |
| --- | --- |
| Hi, I'd like to ask you a few questions. This will only take a few minutes. Please find a quiet and well-lit place and answer each of the questions in as much detail as you can. You can advance questions after 10 seconds but please feel free to speak longer if you have more to say. | This is the introductory text that is shown when the interactive task begins. The task begins once the subject presses Next. |
| Can you please tell me what you have been doing for the past few hours? | This is the first of four open-ended questions. These are meant to capture spontaneous facial expressivity and free speech behavior in response to a neutral question. |
| What are your plans for the rest of the day? | This is the second of four open-ended questions. These are meant to capture spontaneous facial expressivity and free speech behavior in response to a neutral question. |
| Can you tell me about a recent stressful event and how you dealt with it? | This is the third of four open-ended questions. This is meant to capture spontaneous facial expressivity and free speech behavior in response to a negatively valenced question. |
| Can you tell me about a recent positive event and why it was a positive experience? | This is the fourth of four open-ended questions. This is meant to capture spontaneous facial expressivity and free speech behavior in response to a positively valenced question. |
| Please describe what you see in this picture in as much detail as you can and talk about how it makes you feel. | This prompt is shown three times; once each with a positively valenced image, a neutrally valenced image, and a negatively valenced image. The images have been shown to elicit positive, neutral, and negative emotional responses respectively in a large, heterogeneous population. The prompts are meant to capture facial expressivity and free speech behavior in response to positive, neutral, and negative stimuli. |
| Okay. Can you please smile for me and hold the smile for 5 seconds? | This is asking the subject to express and sustain a smiling face for a few seconds. It allows for derivation of evoked facial expressivity for a positive emotion. |
| Can you please make a sad face for me and hold the sad face for 5 seconds? | This is asking the subject to express and sustain a sad face for a few seconds. It allows for derivation of evoked facial expressivity for a negative emotion. |
| Can you please say 'aaahhh' out loud for 3 seconds? | This is asking for sustained phonation of a vowel. It allows for derivation of acoustic properties of voice that have been shown to distinguish disease severity in individuals with Schizophrenia. |
| Thank you! | This is the final prompt. After this, the app displays a dialogue box that confirms that the participant has completed the task. | the subject responds by inputting or selecting a number, e.g., by scoring their emotional state on a scale from 1 to 10.

In some implementations, a single session includes a directed question and/or another type of stimulus (e.g., a subject interview). Table 2 shows an example of a session that includes a combination of directed questions, subject interview stimuli, and facial expression stimuli. This example session includes a subject interview stimulus, two directed questions, and a facial expression stimulus. In some implementations, the stimuli are ordered in an order that is more likely to give reliable results.

TABLE 2

Session with multiple stimulus types

| Displayed Text | Stimulus Type |
| --- | --- |
| Hello. What have you been doing for the past 2 hours? | Subject interview stimulus |
| How much are you enjoying it (on a scale from 1 to 10)? | Directed question |
| How interesting is it to you (on a scale from 1 to 10)? | Directed question |
| Can you please make a sad face for me and hold the sad face for 5 seconds? | Facial expression stimulus |

Subject response data obtained in response to the session of Table 2 can be used to computationally calculate biomarkers, as explained in more detail below. The session of Table 2 also produces two answer selections, one for each of the two directed questions.

In some implementations, answers to directed questions are combined with computationally derived biomarkers in order to obtain a disease severity level. For example, in the session of Table 2, video-recorded subject responses to the EMA and FEE are computationally analyzed to obtain respective numbers on a scale of 1 to 10 (these numbers may reflect any one of a multitude of biomarkers, as described below). Next, response numbers from each stimulus are added together to obtain a disease severity level on a scale of 4 to 40. A disease severity level above 30 indicates that the subject (for example) suffers from Schizophrenia, while a disease severity level below 20 indicates that the subject does not suffer from Schizophrenia. A disease severity level between 20 and 30 indicates that further subject testing is necessary.

The previous, simple example was merely exemplary. In some implementations, answers to directed questions and biomarkers are predictive features in a machine learning model that produces, as an output, a disease severity level. Examples of such machine learning approaches can be found in, for example, Gao et al. (Gao, C., Sun, H., et al. *Model-based and Model-free Machine Learning Techniques for Diagnostic Prediction and Classification of Clinical Outcomes in Parkinson's Disease* (2018) Scientific Reports 8:7129).

A disease severity level based on both biomarkers and answers to directed questions may reflect a more accurate assessment of disease presence and/or severity than either the biomarkers or the answers to directed questions by themselves.

For example, a subject may answer questions untruthfully (e.g., the subject may say that they have been happy, when in fact they have not been happy). A typical automated system relying only on directed questions would accept that answer and, as a result, potentially misdiagnose disease in the subject. However, when computationally derived biomarkers are also derived based on, e.g., video and/or audio of the patient, as in implementations according to the present disclosure, the true emotional state of the subject may be determined and untruthful responses may be identified.

In some implementations, a disease severity level is derived based only on biomarkers. Because a single session may contain multiple types of stimuli, each stimulus allowing for the derivation of one or more biomarkers, a disease severity level may be derived based on multiple types of biomarkers, e.g., both facial behavior biomarkers and speech biomarkers. Such derived disease severity levels may be more indicative of disease level or presence than any single biomarker on its own, or than any disease severity level derived based on only a single type of biomarker.

For example, some biomarkers may be indicative of multiple diseases, such that additional biomarkers are necessary in order to determine the type and/or severity of a disease exhibited by the subject. Using the methods disclosed herein, the biomarkers may be readily extracted from already-obtained subject response data in order to produce a rapid diagnosis. Traditional methods might require significant additional labor and/or time in order to obtain each additional biomarker.

In some implementations, a single set of subject response data (e.g., a subject's response to a single stimulus) is used to calculate multiple biomarkers and multiple types of biomarkers. For example, a video, with recorded sound, of the subject answering a question may be used to calculate both facial feature and verbal biomarkers. Therefore, the methods disclosed herein can be more time-efficient than alternative methods that must obtain separate types of biomarkers separately.

In addition, because, in some implementations, responses to a single stimulus may be used to calculate multiple biomarkers and multiple types of biomarkers, a total number of stimuli that have to be presented may be reduced. This may reduce or eliminate potential negative "path-dependence" effects. For example, for certain sets of stimuli within a single session, the order of the stimuli may have an effect on subject response (e.g., "prime" the subject to respond in a certain way). Or, the length of the session itself may have an effect, e.g., by boring or tiring the subject. By reducing a total number of necessary presented stimuli within a single session, the methods presented herein may lead to more reproducible and reliable subject response data, and thus more useful biomarkers.

In addition, by reducing a total number of necessary presented stimuli within a single session, the methods presented herein may increase the efficiency of a system incorporating the computational analysis unit, for example, by decreasing a number of analyses that must be performed, and/or by allowing the analyses to be performed in detail. For example, given a set of subject response data, processors operating in parallel may derive different biomarkers simultaneously, decreasing overall processing time and causing biomarkers to be available more quickly.

Biomarkers may be derived on a per-stimulus basis or on a per-session basis. For example, a session may include five stimuli and five corresponding sets of subject response data. Some biomarkers may be derived based on all five sets of subject response data—for example, by combining corresponding frame-wise data from the five sets and then performing the biomarker derivation—whereas others may be derived based on a subset of the five sets, e.g., based on only a single set of subject response data, recorded in response to a single stimulus. In some implementations, a biomarker is derived based on subject response to a certain type of stimulus. For example, a biomarker may be derived based on responses to negative stimuli.

In some examples, a biomarker is derived based on a subset of subject response to a single stimulus.

As described in US 2019/0290127 A1, a subject's response to stimuli may be involuntary and/or voluntary. For a certain time period after a stimulus (e.g., 1000 milliseconds, or 500 milliseconds, or 250 milliseconds), the subject's mind and body may present a response to the stimulus, but where the subject has not yet consciously recognized the stimulus, or the subject's response to this stimulus. Beyond this time, thoughtful action takes over and guides the response of the subject. It is this portion of the timeline (and more precisely, the first 250 milliseconds after presentation of the stimulus) that may provide the greatest insight into user response. This unique measurement is not able to be performed manually, as the human vision system is not able to see, recognize and remember facial movements over such a short timeline. Movements of the face in this minimal time frame are referred to as "microexpressions." Essentially, these microexpressions, which are a portion of the "facial behavior" described herein, are presented by the face of the subject before the subject is fully cognitive of and able to process the received stimulus.

This disclosure has described active tasks for the subject to perform, including requests to make a particular vocal output, requests to make a particular facial expression, requests to respond to an image, and requests to answer a question. These active tasks may provide advantages over passive tasks, such as wearing a step-counter or measuring smartphone keystroke activity, at least because the active tasks can be specifically designed to elicit subject responses that are particularly amenable to biomarker derivation.

For example, asking a subject for a sustained vowel phonation may allow for derivation of specific verbal biomarkers (e.g., a range of fundamental frequencies exhibited in the phonation) that may be less useful if derived from free speech. The particular stimulus presented to the subject makes it more likely that the subject response data will be useful.

For example, asking a subject to hold a smile may allow for detection of facial tremor that would be less obvious in observations of normal (e.g., un-stimulated) subject activity.

For example, showing a subject a negatively-valenced image may evoke a stronger subject response, and thus a more reliable biomarker, than would be observed in spontaneous subject behavior.

The combination into a system of a display (to present stimuli), a controller (to control the display of the stimuli), a capture device (to capture subject responses), and a computational analysis unit (to derive quantities based on the subject responses) may provide further advantages. Because each of these components may each be coupled to any or all of the other components, the computational analysis unit, as described above, may obtain information about the stimuli presented, and analyses applied to the subject response data might be chosen to be most efficient and indicative of disease, based on the presented stimuli.

A further potential advantage of the methods and systems disclosed herein is that the computational analysis unit and/or the controller may send instructions for stimuli (to the controller or to the display) based on data about the subject. Because, as described below, certain biomarkers indicate disease severity levels for particular diseases, and because, as described above, certain stimuli generate subject responses that are more informative and useful for deriving particular biomarkers, the computational analysis unit and/ or the controller may, based on data indicating the subject may have a particular disease, send instructions to present a stimulus that will generate a subject response usable for derivation of a biomarker indicative of a disease severity level of the disease.

For example, the computational analysis unit and/or the controller may determine, based on subject data, that the subject may suffer from Schizophrenia. As described below, the verbal fundamental frequency generated by the subject may be an effective biomarker of Schizophrenia. Therefore, the computational analysis unit and/or the controller may transmit an instruction to present a stimulus requesting a sustained vowel phonation, from which, as described above, a fundamental frequency range may be more reliably extracted than from unstructured verbal output.

Figure 4:
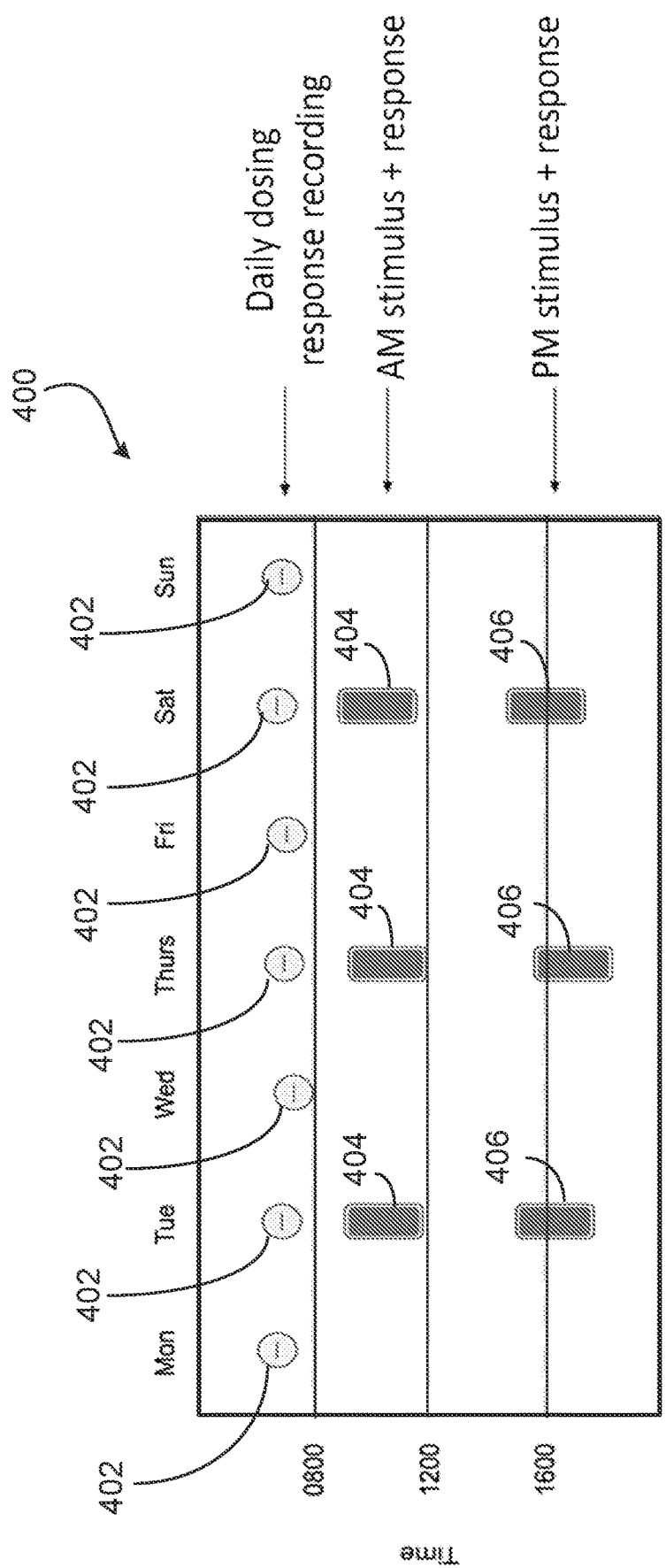
FIG. 4 is an exemplary session schedule

In some implementations, as shown in FIG. 4, sessions are scheduled across or within days. In the schedule 400, three sets of sessions are shown. In the "daily dosing response recording," with scheduled sessions 402, the subject is asked to record themselves taking a medication.

The "AM stimulus+response" is a session that must be completed in the morning, as shown by the scheduled morning windows 404. The session itself may be short—for example, five minutes—but must be done within the windows 404. Similarly, the "PM stimulus+response" must be performed in the corresponding evening windows 406.

Although FIG. 4 shows every-other-day stimulus and response sessions, in some implementations a given type of session might be performed daily, or even more than once per day.

In some implementations, the frequency of sessions determines the temporal granularity of the data obtained, and can depend on the specific circumstances of the subject. For example, if subject response data is recorded in order to test the effects of a medication, a slow-acting treatment compound in a relatively long study may feature a less frequent schedule of sessions than a fast-acting treatment compound in a shorter study, where one may be interested in measuring changes in disease characteristics within hours or days after dosing.

Frequency of sessions may also depend on the disease that the biomarkers indicate. For example, a schedule for determining a severity of Parkinson's disease may include two sessions per day.

In some implementations, each session is less than two minutes, less than five minutes, or less than ten minutes.

In some implementations, sessions to measure the presence of a given disease are performed weekly, every-other-day, daily, or twice daily, frequencies which might not be feasible for traditional doctor-performed tests. In some implementations, sessions are performed at least daily for more than a week.

Biomarkers can be divided up, broadly, into three categories, these being facial behavioral characteristics, verbal characteristics, and speech characteristics. Oculomotor behavior, or behavior related to the motion of the eye, can be a potential fourth category. Oculomotor behavior may be analyzed in a manner analogous to that described for facial movement behavior below.

Facial expressivity has been shown to be indicative of clinical functioning across patient populations. This includes individuals with schizophrenia (Gottheil, E., Thornton, C., Exline, R., *Appropriate and Background Affect in Facial Displays of Emotion Comparison of Normal and Schizophrenic Males* (1976) Arch Gen Psych 33(5)), major depressive disorder (Berenbaum, H., Oltmanns T., *Emotional experience and expression in schizophrenia and depression*

(1992) J. Abnorm. Psychol. 101(1)), Parkinson's Disease (Katsikitis, M., Pilowsky, I., *A study of facial expression in Parkinson's disease using a novel microcomputer-based method* (1988) J Neurol. Neurosurg. Psychiatry 51(3)), and several other patient populations (Harrigan, J., O'Connell, D., *How do you look when feeling anxious? Facial displays of anxiety* (1996) Personality and Individual Differences 21(2)).

Traditionally, facial expressivity has been manually coded through the Facial Action Coding System (FACS, see Ekman, P., Rosenberg, E., *What the Face Reveals: Basic and Applied Studies of Spontaneous Expression Using the Facial Action Coding System* (1997)) by human raters. This method can be subjective, time-consuming, and is limited by a lack of detailed spatial and temporal information. It can also be impractical to deploy manual coding of facial expressivity in large patient populations. Computational analysis of facial behavior, as described here, can allow for the measurement of facial expressivity with high accuracy.

Biomarkers on expressivity of happiness, sadness, anger, fear, disgust, surprise, and contempt are derived from videos collected through responses to carefully pre-designed stimuli. The videos are analyzed to extract emotion-labeled subject descriptor time series. In some implementations, prevalence and patterns of activity for each emotion are derived over time. Subject descriptors capturing facial expressivity can be used to study the progression of an individual or clinical population over time as they receive treatment, distinguish between healthy individuals and patient populations, and distinguish between individuals receiving treatment and those receiving placebo medication. In some implementations, facial expressivity time series measure facial expressivity as it relates to specific emotions, the prevalence of those emotions, and the patterns in which they occur.

In another example, recorded subject facial behavior data may be processed to extract tremor-labeled subject descriptor time series. Typical assessments of disease severity in individuals with movement disorders such as Parkinson's disease or essential tremor depend on in-person evaluations by clinicians (Stacy, M., Hauser, R., *Development of a Patient Questionnaire to facilitate recognition of motor and non-motor wearing-off in Parkinson's disease* (2007) Journal of Neural Transmission 114(2)). These assessments can require significant time and effort from patients and clinicians and have been shown to be subjective and inaccurate in their evaluation of disease severity (Siderowf A., McDermott M., Kieburtz K., Blindauer K., Plumb S., Shoulson I.; *Test-retest reliability of the unified Parkinson's disease rating scale in patients with early Parkinson's disease: results from a multicenter clinical trial* (2002) Mov. Disord. 17(4)). These assessments can have low inter-assessor reliability.

Verbal tremor has also been linked to multiple diseases. Computational analysis of facial and verbal tremor behavior, as described here, can allow for accurate measurements of disease severity at higher frequencies or on larger populations without significant burden on the patients or clinicians, while allowing the derived measurements to be more accurate, reliable, and/or stable.

Biomarkers capturing facial tremor are derived based on video and audio of subject response to pre-designed stimuli. The biomarkers can then be used to study the progression of movement characteristics in a subject over time as they receive treatment, distinguish severity of tremor between healthy subjects and patient populations, and distinguish severity of tremor between subject receiving treatment and those receiving placebo medications.

In some implementations, for each frame of video captured (i.e., for each unit of subject response data) a facial analysis system (e.g., OpenFace) is used to detect and crop the face of the subject being exposed to stimuli, ensuring that the spatial positioning of the face remains consistent across frames. OpenFace (https://cmusatyalab.github.io/openface) may perform facial analysis based on identification of predetermined facial points, as described below. The facial analysis system also calculates a confidence score to ensure that the image it is cropping is indeed a face: only images with an 80% confidence score or above are selected for further analysis. After the face has been cropped and positioned, deep neural networks and/or other machine learning methods are used to label facial musculature in each frame. This allows detection of action units according to the FACS. The action unit detection process may be implemented in part as described below.

FACS defines a set of facial musculature movements—or action units—that collectively are able to describe nearly all possible facial expressions. For each frame, the computational analysis unit outputs whether or not an action unit is present as well as a 5-point score on the expressivity of that action unit. These are frame-wise subject descriptors, as described above. Combining the frame-wise data creates time series of all the action units as well as the degree to which they are being expressed. This extracted information is no longer identifiable to the subject and hence is not considered Protected Health Information or otherwise personally identifiable information. In some implementations, subsequent analyses are done to this dataset, rather than to the videos themselves.

In some implementations, to detect action units, multiple points on the face of a subject are defined and analyzed. While any particular points may be defined, the number and location of the points may be selected based on the desired attributes of the user to analyze. For example, a certain number and location of points may allow for robust tracking of action units of the face, and thus provide the ability to analyze facial expression without overwhelming the computational analysis unit. Each of these points may be measured to determine its movement during response to the presentation of one or more stimuli to the subject. As is known in the art, when a particular point moves (action units may comprise movement of a single or multiple points, keypoints or landmarks), it is possible to measure this movement. However, if point(s) of the action unit moves too far from an expected "neutral" location, the system breaks down and the action unit cannot be recognized. However, rather than using as a "neutral" location system an average mask across all subject, the system of the present disclosure relies on a more customized mask for each individual subject. Thus, by setting a baseline positioning of the action units of a particular subject, it is possible to better account for differences between the face of a particular individual.

Such a baseline position may be defined by providing a basic set of images or other material to a subject and measuring the response of the predefined facial points. By presenting this consistent "calibration" set of images or other stimuli it is possible to then determine an expected movement of the points, and then determine a relative movement when further unique or different images or stimuli are provided. This allows for a subject with relatively low action unit magnitude (e.g., movement of facial points) to be judged against this expectation, while an animated person will be judged against this more animated expectation. Thus, the expected movements may also be tied to a particular individual, thus allowing for more flexibility in tracking the action units as the subject is provided with one or more stimuli.

Also, it has been discovered that it is possible to identify which of the presented action units (or other appropriate measurement points or values, including but not limited to keypoints, landmarks (in some implementations comprising one or more points on the face of a subject that may be indicative of movement of the face that may be of interest, typically indicative of changes in facial expression), shapes, textures, poses, features from both 2D and 3D sensors) are most likely to be important when reviewing progressions for a particular disease or symptom, for example. Based upon the desired action units, it may be useful to focus on only these action units, and not measure the others. Thus, a context-sensitive system may be provided in which a priori knowledge about a particular therapeutic area or disease state may allow for the focusing of the system on the action units most likely to give valuable information.

Action units and their expressivity in each frame, types of subject descriptors, can be used to calculate facial expressivity, a further subject descriptor, as it relates to specific emotions for each frame (Ekman, P., Levenson, R. W., & Friesen, W. V. (1983). *Autonomous nervous system activity distinguishes among emotions* Science, 221(4616)). This leads to several time series on emotional expressivity for the subject. Those time series can then be used to calculate biomarkers, e.g., the prevalence of each emotion over time as well as their patterns of occurrence.

Figure 5:
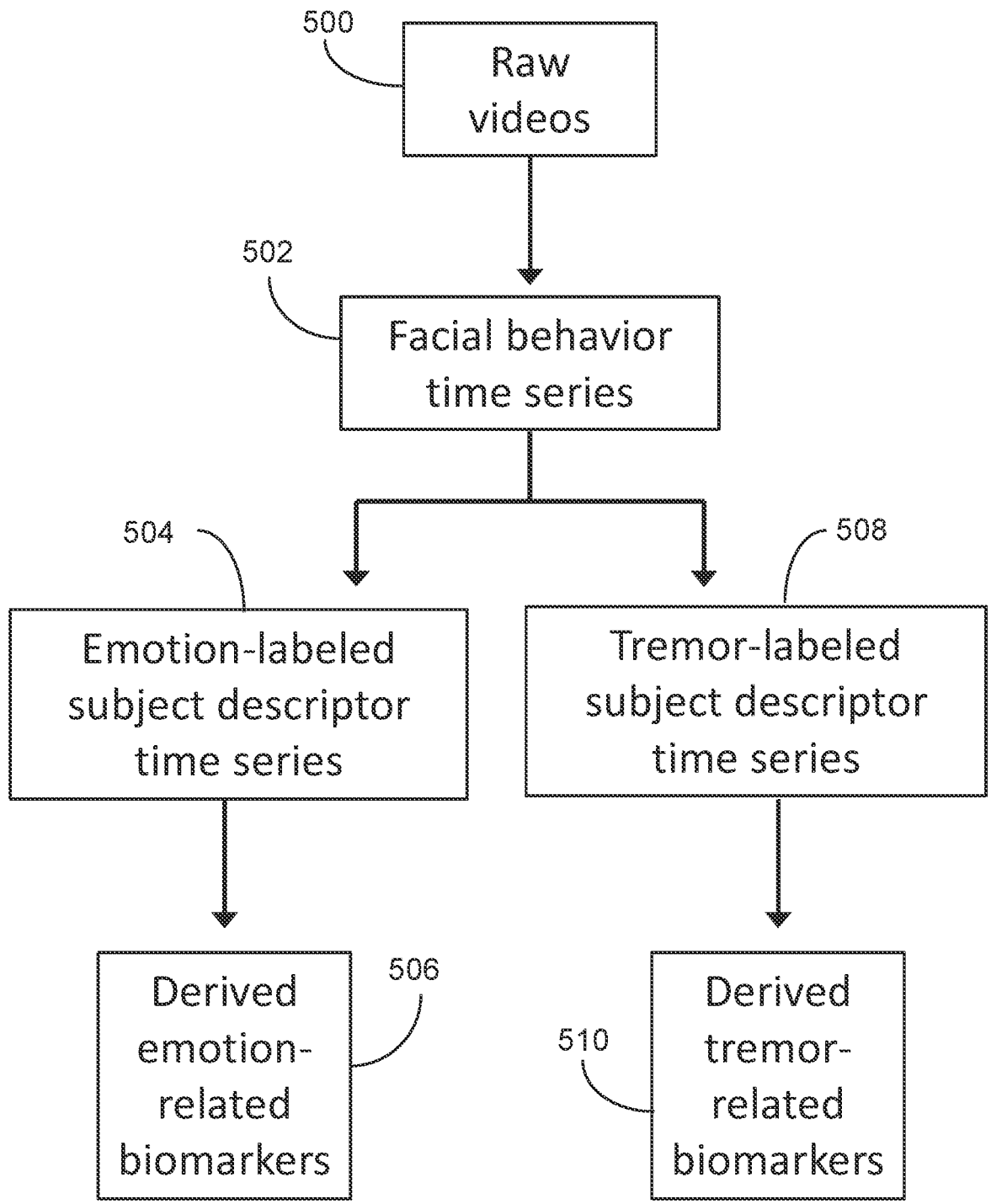
FIG. 5 is a flow chart of exemplary facial behavior data processing

An example pipeline for derivation of derived facial feature biomarkers is shown in FIG. 5. The process starts with video 500 of subject response to stimuli. Based on these, facial musculature movement time series 502 are derived. As described above, for an example facial musculature movement time series 502 might be a time series describing, for each frame, an extent to which a particular facial muscle is contracted These are converted into emotion-labeled time series 504, which allow for the derivation of derived emotion-related biomarkers 506.

In some implementations, to calculate emotion-related subject descriptors, for each frame of video, several initial subject descriptors are extracted: a binary variable of whether facial behavior associated with the emotion is detected, and a continuous variable indicating an intensity for each action unit. Sadness, for example, is detected by looking for an "inner brow raise," a "brow lower," or a "lip corner depress" (Ekman P., Friesen W., *Facial Action Coding System: A Technique for the Measurement of Facial Movement* (1978))

If the binary variable for the frame indicates emotion detection, the continuous variables of each frame are summed and normalized to give a frame-wise subject descriptor of sadness intensity, face_sad_exp. The binary and continuous variables may be extracted using, for example, OpenFace, using methods like those described above.

Biomarkers may be derived based on the emotion-related subject descriptors. For example, the biomarker face_sad_exp_mean is the average value of face_sad_exp over all frames of data. face_sad_exp_mean_posimg, face_sad_exp_mean_neuimg, and face_sad_exp_mean_negimg are the averages of face_sad_exp in response to positively, neutrally, and negatively valenced image stimuli, respectively. Specifically, they are the averages of face_sad_exp over the frames in which the subject is responding to those respective stimuli. face_sad_exp_mean_sad_and_face_sad_exp_mean_maxsad are the averages of face_sad_exp in frames when the subject is asked first to make a sad face and then to make a really sad face. face_sad_exp_mean_max is the average of face_sad_exp in frames when the subject is asked to make the most expressive face they can.

Analogous biomarkers may be derived for other emotions, including happiness, disgust, fear, anger, and contempt. Subject descriptors for individual emotions may also be combined in order to calculate biomarkers based on multiple emotions simultaneously.

The facial musculature movement time series also allows for the derivation of derived tremor-related biomarkers, with methods analogous to those used for the derived emotion-related biomarkers. Based on the facial behavior time series 502, a tremor-labeled subject descriptor time series 508 is generated, and then derived tremor-related biomarkers 510 are derived.

Speech and verbal behavior is another realm of subject analysis. These have been shown to be indicative of clinical functioning across patient populations. This includes individuals with schizophrenia (Bedi, G., Facundo, C., Cecchi, G., Slezak, D., Sigman, M., Mota, N., Ribeiro, S., Javitt, D., Copelli, M., Corcoran, C., *Automated analysis of free speech predicts psychosis onset in high-risk youths* (2015) NPJ Schizophrenia), major depressive disorder (Cohn, J., Kruez, T., Matthews, I., Yang, Ying., Nguyen, Minh., Padilla, M., Zhou, F., De la Torre, F., *Detecting depression from facial actions and vocal prosody* (2009) 2009 3rd International Conference on Affective Computing and Intelligent Interaction and Workshops), Parkinson's Disease (Ho, A., Bradshaw, J., Iansek, R., Alfredson, R., *Speech volume regulation in Parkinson's disease: effects of implicit cues and explicit instructions* (1999) Neuropsychologia 37(13)) and several other patient populations.

Verbal features and content of speech are typically assessed during in-person assessments of clinical functioning. However, such assessments can be subjective, tedious, and are impractical to conduct in large populations. The methods disclosed herein can allow for the derivation of derived verbal and biomarkers more reliably, at higher frequency, and/or across a larger population, for instance, remotely.

Biomarkers capturing verbal behavior and content of speech are captured through a subject's responses to pre-designed stimuli. Verbal and speech behavior that is captured can be used to study the progression of the subject or a clinical population over time as they receive treatment, distinguish between healthy individuals and patient populations, and distinguish between individuals receiving treatment and those receiving placebo medication.

Figure 6:
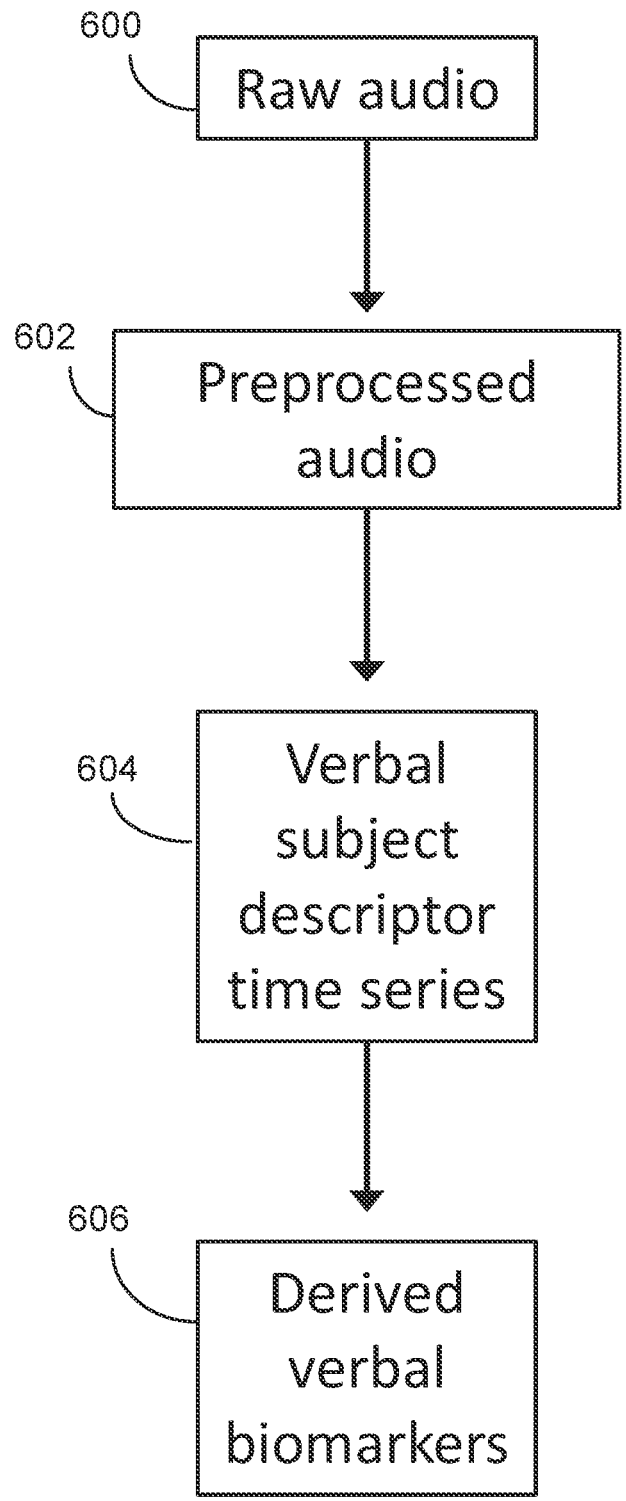
FIG. 6 is a flow chart of exemplary verbal data processing

FIG. 6 shows one embodiment of a process for calculating derived verbal biomarkers. First, raw audio data 600 is collected from a subject in response to stimuli. The audio is then preprocessed into preprocessed audio data 602. Preprocessing may include, for example, frequency filtering and/or noise reduction, and may be performed using, for example, logmmse (https://pypi.org/project/logmmse/) .logmmse and analogous systems use frequency-domain analysis (e.g., via a Fourier transform of input raw audio data) to implement a minimum mean-square error log-spectral amplitude estimator and thereby reduce noise in recorded speech.

The preprocessed audio is processed to derive verbal subject descriptors 604. Extraction of these quantities may performed using, for example, Parselmouth/Pratt (https://pypi.org/project/praat-parselmouth, http://www.fon.hum.uva.nl/praat/). These and analogous systems can take, as input, an audio file, and produce, as output, spectrograms and analyses of the audio. These analyses can include, for example, spectral analysis, pitch analysis, formant analysis, and intensity analysis.

Each verbal subject descriptor or set of verbal subject descriptors allows the derivation of one or more derived verbal biomarkers.

One verbal subject descriptor is the fundamental frequency, $F_0$. $F_0$ is the lowest frequency of a periodic waveform, measured in Hertz. It is the greatest common divisor of all the frequency components contained in a signal. Signal decomposition, as referenced elsewhere herein, may refer to at least decomposing an audio signal into constituent frequencies and identifying quantitatively a fundamental frequency of the signal.

Speech affected by depression shows reduced $F_0$ mean and range during sustained vowel production (Breznitz, Z., *Verbal indicators of depression* (1992) The Journal of general psychology 119(4)). Patients with Parkinson's disease tend to show decreased variability in $F_0$, with the effect seeming to normalize once treatment begins (Harel, B., Cannizzaro, M., Snyder, P. *Variability in fundamental frequency during speech in prodromal and incipient Parkinson's disease: A longitudinal case study* (2004) Brain and cognition 56(1)). During oral reading, schizophrenia patients show a significantly larger $F_0$ than healthy controls (Saxman, J., Burk, K. *Speaking fundamental frequency and rate characteristics of adult female schizophrenics* (1968) Journal of speech and hearing research 11(1)).

After extraction of $F_0$ for each frame of audio, several further verbal subject descriptors may be generated. For example, aco_ff is a vector of frame-wise fundamental frequencies, and aco_voiceLabel is a vector of frame-wise binary variables indicating voicedness. In some implementations, the fundamental frequency is the lowest frequency of the harmonic pattern of the audio. In some implementations, the voicedness is a measure of the "buzziness" of the audio, as determined by spectral analysis.

Next, verbal biomarkers 606 can be derived. For example, aco_ff_mean is the average fundamental frequency across all audio frames, and aco_ff_skew is the skewness of the fundamental frequency across all audio frames.

Another verbal subject descriptor is the jitter. The jitter of an audio signal is the parameter of frequency variation from cycle to cycle, and is affected mainly by the lack of control over vocal cord vibration.

Increased jitter during sustained vowel sounds has been shown to correlate positively with depression (Ozdas, A., Shiavi, R., Silverman, S., Silverman, M., Wilkes, D., *Investigation of vocal jitter and glottal flow spectrum as possible cues for depression and near-term suicidal risk* (2004) IEEE Trans. Bio-Eng. 51). Parkinson's patients show increased jitter during sustained vowels as compared to healthy controls (Little, M., McSharry, P., Hunter, E., Spielman, J., Ramig, L. *Suitability of dysphonia measurements for telemonitoring of Parkinson's disease* (2008) Nature Precedings, 1-1). Schizophrenia patients show increased jitter during natural speech as compared to healthy controls (Kliper, R., Portuguese, S., Weinshall, D. *Prosodic analysis of speech and the underlying mental state* (2015) International Symposium on Pervasive Computing Paradigms for Mental Health).

aco_jitter may be extracted as a vector of frame-wise jitter during voiced frames only. Then, derived verbal biomarkers such as aco_jitter_stdev, the standard deviation of the jitter across all voiced frames, can be derived.

Glottal-noise-excitation ratio (GNE) is an indirect measure of breathiness. Parkinson's patients show signification reduction in GNE mean and a significant increase in GNE standard deviation as compared to controls (Zhang, H., Yan, N., Wang, L., Ng, M., *Energy distribution analysis and nonlinear dynamical analysis of phonation in patients with Parkinson's disease* (2017) 2017 Asia-Pacific Signal and Information Processing Association Annual Summit and Conference IEEE). vrbl_gner, a frame-wise measure of this ratio, may be derived according to the methods outlined in Michaelis et al. (Michaelis, D., Gramss, T., Strube, H. W., *Glottal-to-Noise Excitation Ratio—a New Measure for Describing Pathological Voices* (1997) Acustica 83).

Derived verbal biomarkers may be derived based on vrbl_gner. For example, average glottal-to-noise excitation ratio, vrbl_gner_mean, is the average of the raw verbal variable glottal-to-noise excitation ratio over all audio frames in a given set of audio frames. vrbl_gner_mean_vowel_x is the average glottal-to-noise excitation ratio when the subject is asked to sustain vowels sounds for the vowels a, e, i, o, and u, with x in the variable name denoting the vowel. vrbl_gner_mean_posimg, vrbl_gner_mean_neuimg, and vrbl_gner_mean_negimg are the average glottal-to-noise excitation ratio values in verbal responses to positively, neutrally, and negatively valenced images, respectively.

Figure 7:
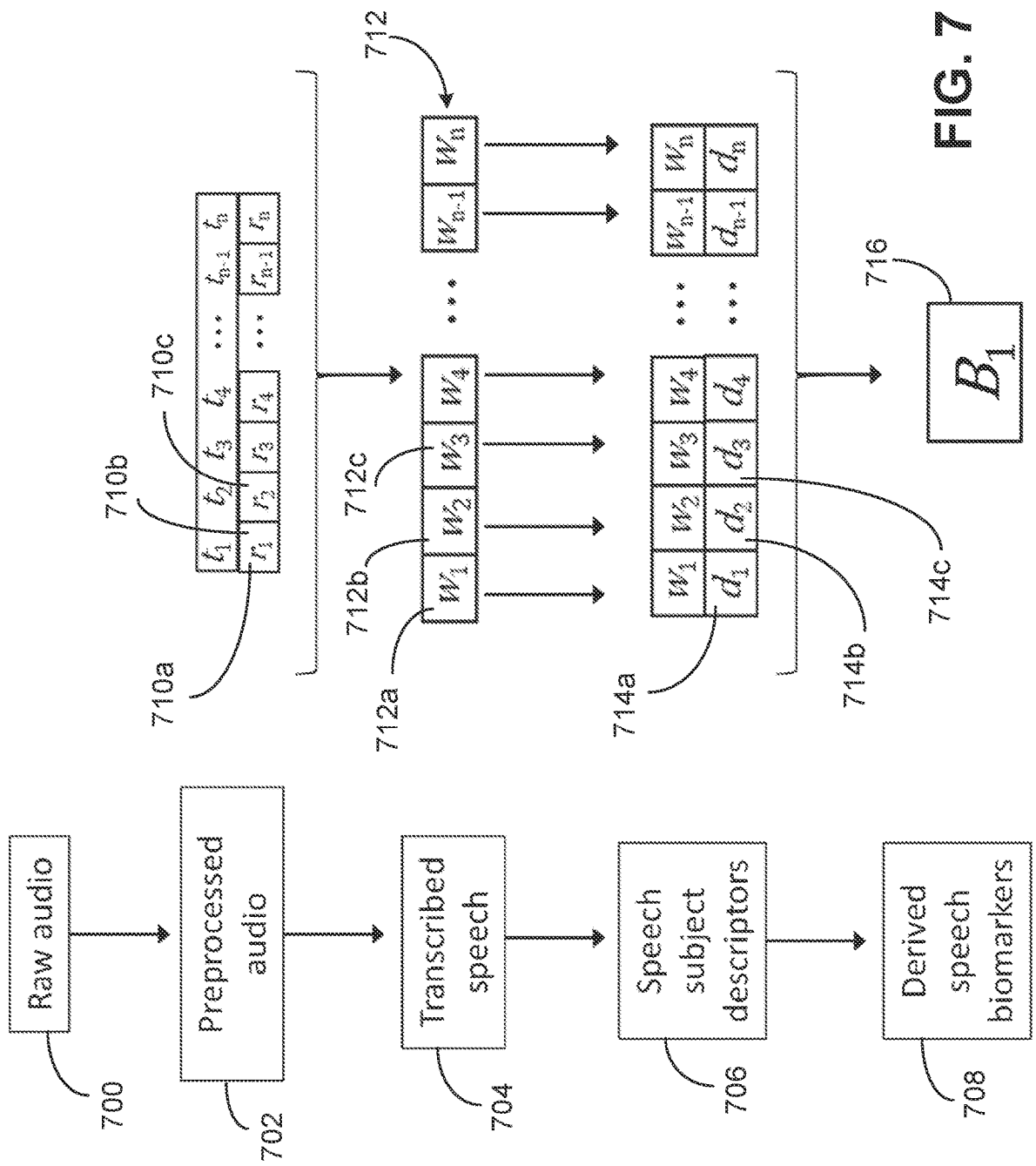
FIG. 7 is a flow chart and block diagram of exemplary speech data processing

FIG. 7 shows one embodiment of a process for calculating derived speech biomarkers. First, audio data 700 is collected from a subject in response to stimuli. The audio is then preprocessed into preprocessed audio data 702. Preprocessing may include, for example, frequency filtering and/or noise reduction, and may be performed using, for example, logmmse.

The preprocessed audio data is transcribed into transcribed speech 704. This transcription may be performed using, for example, Amazon Transcribe (https://aws.amazon.com/transcribe/). Amazon Transcribe and analogous systems use deep-learning methods to convert speech to text. Based on the transcribed speech 704, speech subject descriptors 706 are derived.

In some implementations, unlike facial subject descriptors and verbal subject descriptors, speech subject descriptors are not derived for each video or audio frame. Rather, they are derived for each word that is transcribed, or for sequences of words (e.g., for each phrase or for each sentence). Hence, in some implementations, a speech subject descriptor vector for an audio file will have a length equaling the number of words (or phrases, or sentences, etc.) that were transcribed from that audio file instead of the number of frames in that audio file.

For example, speech subject descriptors 706 may include nlp_start_times and nlp_end_times, vectors giving the start and stop time-points, respectively, of each transcribed word. The length of each vector is equal to the number of transcribed words (or phrases, or sentences, etc.).

In the implementation of FIG. 7, preprocessed subject response data (e.g., 710a, 710b, 710c) is processed to generate transcribed speech, each unit of transcribed speech (e.g., 712a, 712b, 712c) being a single word. Then, speech subject descriptors (e.g., 714a, 714b, 714c), each corresponding to a respective word 712, are derived (in some implementations, each word 712 corresponds to multiple speech subject descriptors).

Transcribed speech may be analyzed to identify individual sentences within the speech, and analysis may be done on a per-sentence basis. Transcribed speech may be analyzed to identify individual phrases or clauses within the speech, and analysis may be done on a per-phrase/clause basis.

As another example, nlp_pos_prob is a vector containing, for each transcribed word, the probability that the word conveys a positive sentiment. In some implementations, sentiment analysis is carried out user the VADER Sentiment Analysis tool (https://github.com/cjhutto/vaderSentiment). The VADER Sentiment Analysis tool uses a sentiment lexicon to evaluate both the polarity (e.g., positive or negative) and intensity of sentiments expressed in text.

Analogous speech subject descriptors may be extracted for other sentiments (e.g., negative sentiment).

As another example, nlp_partsOfSpeech is a vector containing, for each transcribed word, the part of speech of the word.

Speech characteristics have been linked to disease occurrence and severity. For example, Alzheimer's disease patients have been reported to produce more pronouns, verbs, and adjectives, and fewer nouns (Jarrold, W., Peintner, B., Wilkins, D., Vergryi, D., Richey, C., Gorno-Tempini, M., Ogar, J. *Aided diagnosis of dementia type through computer-based analysis of spontaneous speech.* (2014) Proceedings of the Workshop on Computational Linguistics and Clinical Psychology: From Linguistic Signal to Clinical Reality). Major Depressive Disorder has been linked to altered pronoun usage and sentence order (e.g., verb before noun) (Trifu, R., Nemes, B., Bodea-Hategan, C., Cozman, D. *Linguistic Indicators of Language in Major Depressive Disorder (MDD). An Evidence Based Research* (2017) Journal of Evidence-Based Psychotherapies 17(1)). Alzheimer's patients, Parkinson's patients, Schizophrenia patients, and depressed patients have been shown to repeat words more often than healthy control patients (Guinn, C. I., Habash, A. *Language analysis of speakers with dementia of the Alzheimer's type* 2012 AAAI Fall Symposium Series; Cozolino, L. *The oral and written productions of schizophrenic patients* (1983) Progress in Experimental Personality Research, 12). Depressed patients and Schizophrenia patients tend to produce more negatively-valenced speech than healthy control patients (Rude, S., Durham-Fowler, J., Baum, E., Rooney, S., Maestas, K., *Self-report and cognitive processing measures of depressive thinking predict subsequent major depressive disorder* (2010) Cognitive Therapy and Research, 34(2)). Alzheimer's patients and Schizophrenia patients are known to use fewer subordinate clauses than healthy control patients (Croisile, B., Ska, B., Brabant, M., Duchene, A., Lepage, Y., Aimard, G., Trillet, M. *Comparative study of oral and written picture description in patients with Alzheimer's disease* (1996) Brain and language, 53(1)) (DeLisi, L. *Speech disorder in schizophrenia: review of the literature and exploration of its relation to the uniquely human capacity for language* (2001) Schizophrenia bulletin, 27(3)).

Based on these known relationships, related speech biomarkers 708 are derived based on the speech subject descriptors 706. For example, nlp_pronounsPerAns, nlp_pronounsPerSen, and nlp_pronounsPerWrd are derived speech biomarkers indicating average numbers of pronouns per, respectively, response, sentence, and word. nlp_sentiment_mean is a derived speech biomarker indicating average sentence valence (e.g., an average positivity of the sentences). nlp_subClausesPerSen is a derived speech biomarker indicating an average of the number of subclauses per sentence in a response. nlp_pos_prob_mean is the average positive sentiment probability in the absence of stimuli with a specific valence. nlp_pos_prob_mean_posimg is the average positive sentiment probability in response to positively valence images.

In the implementation of FIG. 7, the derived speech biomarker 716 is derived based on the speech subject descriptors 714.

Pause length and pause count are features that straddle the verbal and speech categories. Depressive disorder and Schizophrenia have been shown to correlative positively with increased pause measures, while Parkinson's disease patients tend to show a significant reduction in the number of pauses produced during speech (Alpert, M., Pouget, E., Silva, R., *Reflections of depression in acoustic measures of the patient's speech* (2001) Journal of affective disorders, 66(1); Skodda, S., Schlegel, U., *Speech rate and rhythm in Parkinson's disease* (2008) Movement disorders: official journal of the Movement Disorder Society, 23(7); Rapcan, V., D'Arcy, S., Yeap, S., Afzal, N., Thakore, J., Reilly, R., *Acoustic and temporal analysis of speech: A potential biomarker for schizophrenia.* Medical engineering & physics, 32(9)).

Using subject response descriptors such as frame voice, a frame-wise binary vector indicating whether or not speech is detected in the given frame, biomarkers are derived. Such biomarkers may include vrbl_voice, the proportion of total frames that include speech, and nlp_numPauses, the number of pauses in the subject response.

As described above, biomarkers, once derived, may be used to determine a disease severity level. The determination may incorporate a machine learning process in which the biomarkers are inputs. The machine learning process may use previous data (e.g., data of disease severity and biomarkers of other subjects) to train a machine learning algorithm that evaluates new subjects' biomarkers. Machine learning algorithms might be designed based on clinical research knowledge. For example, it was described above that Alzheimer's patients have been shown to repeat words more often than healthy control patients. Therefore, a biomarker indicating word repetition rate (the biomarker being based on subject descriptor data derived from transcribed speech subject response data) may be an input to an Alzheimer's specific machine learning process that also takes, as inputs, the subject's age, other speech biomarkers of the subject, verbal biomarkers of the subject, and facial behavior biomarkers of the subject, for example. An output of the machine learning process may be a level of Alzheimer's severity in the patient.

The example subject descriptors and biomarkers described above (e.g., in reference to FIGS. 5-7) may be implemented in systems according to the present disclosure, e.g., as shown in FIG. 1. Derivation of the variables listed above (e.g., subject descriptors and biomarkers) may be performed by the computational analysis unit 112, which may include multiple individual devices, processors, etc. The video and audio inputs from which the subject descriptors and biomarkers are calculated are recorded by a capture device 108 communicably coupled to the computational analysis unit 112. Based on the one or more derived biomarkers, the computational analysis unit 112 may determine a disease severity level of the subject. The biomarkers and/or the disease severity level may be output from the computational analysis unit 112. For example, the computational analysis unit 112 may transmit the biomarkers and/or the disease severity level to the controller 101 for display on the display 100 that presents stimuli to the subject, or the biomarkers and/or the disease severity level may be output to a separate device.

Biomarkers may be stored on a storage device local to the computational analysis unit, the display, and/or the controller, or on a remote storage device. The storage device may be included in a system along with the computational analysis unit, the display, and/or the controller. In some implementations, biomarkers from multiple sessions across a period of time are analyzed in order to track progression of disease symptoms in a subject, as described further in United States Patent Application Publication 2019/0290129 A1, the entirety of which is incorporated herein by reference. Subject response data, subject descriptors, and/or biomarkers may be collected, stored, and analyzed to create a database that may be indexed by any number of dimensions, including diseased indication.

In some implementations, daily or more frequent subject response data may be captured, and corresponding biomarkers derived, for a baseline determination in order to evolve a baseline for a particular subject. Future data can be compared to this baseline. Furthermore, in addition to providing a custom baseline for each individual subject, by use of the database, it is also possible to compare this baseline to an average baseline across all subjects in order to discern absolute information about the current status of the subject relative to others in the same therapeutic area, or suffering from the same disease, by way of example.

In some implementations, biomarkers are analyzed based on demographic data of the subject, as disclosed in United States Patent Application Publication 2019/0290128 A1, the entirety of which is incorporated herein by reference. In some implementations, biomarkers of many different subjects may be analyzed together using, for example, machine learning methods.

Aspects of a subject's response to medication or a subject's condition may also be predicted based upon the subject demographics and a database of prior subjects' data (subject response data, subject descriptors, and/or biomarkers). Thus, disease symptom progression may be predicted, and may be adjusted based upon expected medication response. Deviation from the expected symptom progression as determined in an automated fashion by the present systems may indicate a parallel deviation from the required medication administration protocol, or an atypical response of the subject to the medication. Further, a predicted impact (i.e. comparing a measured value or values to an expected value or values as determined from prior data captures) on the computational diagnostic measures described above, whether collected actively or passively, may be provided. The results of such an analysis may be converted to an efficacy score, indicative of the effectiveness of the medication based upon the various dimensions of the subject. Values may be combined across measurements into a single score indicative of effectiveness of the medication. Two drugs, one that greatly improves tremor, but does poorly with fine motor control, and another that is the opposite may have similar efficacy scores, because they both improve conditions. The true benefit of the system is to try to recognize the features of the first drug that improve tremor and the features of the second drug that improve fine motor control, and search for a new drug having these two features so that a better drug with higher efficacy score overall can be discovered. Thus, for future subjects, measurement of a number of parameters may allow for the prediction of how effective a medication may be for a particular subject, and ultimately may allow for the selection of one medication over another based upon the demographics or other measurements of the subject, and similarly may be able to predict the response of the subject to the measurements and/or stimuli noted above. Such comparisons may be performed during the entire term of medication administration, and may allow for monitoring of disease progression, and perhaps suggest when changes in medication protocol may be justified. Once accumulated, such a database may be available for use in order to aid in predicting subject response to other medications that may be under development. For example, a scoring system may be created to show effectiveness and safety of a particular medication in comparison to predecessor drugs or other treatment options that have gone through the system when presented with a particular disease or therapeutic area. Additionally, a measured response of subjects to a particular drug may allow for prediction as to how similarly-situated subjects may respond to another drug, or alternatively, how other subjects may respond to the same drug. Through analysis, other subjects having similar responses on one or more particular dimensions may allow for prediction of successful response to the drug, for example. In this manner, predictability of response to a drug may be available based upon similarity of subjects on the most critical dimensions.

Therefore, in accordance with the various embodiments of the disclosure, improved methods and systems are provided for presenting stimuli to a subject, for analyzing collected subject response data, and for deriving biomarkers indicative of a level of disease severity.

All or part of the processes described herein and their various modifications (hereinafter referred to as "the processes"), including the controller, the display, the computational analysis unit, and the capture device can be implemented, at least in part, via a computer program product, i.e., a computer program tangibly embodied in one or more tangible, physical hardware storage devices that are computer and/or machine-readable storage devices for execution by, or to control the operation of, data processing apparatus, e.g., a programmable processor, a computer, or multiple computers. A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a network.

Actions associated with implementing the processes can be performed by one or more programmable processors executing one or more computer programs to perform the functions of the calibration process. All or part of the processes can be implemented as, special purpose logic circuitry, e.g., an FPGA (field programmable gate array) and/or an ASIC (application-specific integrated circuit). Other embedded systems may be employed, such as NVidia® Jetson series or the like.

Processors suitable for the execution of a computer program include, by way of example, both general and special purpose microprocessors, and any one or more processors of any kind of digital computer. Generally, a processor will receive instructions and data from a read-only storage area or a random access storage area or both. Elements of a computer (including a server) include one or more processors for executing instructions and one or more storage area devices for storing instructions and data. Generally, a computer will also include, or be operatively coupled to receive data from, or transfer data to, or both, one or more machine-readable storage media, such as mass storage devices for storing data, e.g., magnetic, magneto-optical disks, or optical disks. Processors "configured" to perform one or more of the processes, algorithms, functions, and/or steps disclosed herein include one or more general or special purpose processors as described herein as well as one or more computer and/or machine-readable storage devices on which computer programs for performing the processes are stored.

Tangible, physical hardware storage devices that are suitable for embodying computer program instructions and data include all forms of non-volatile storage, including by way of example, semiconductor storage area devices, e.g., EPROM, EEPROM, and flash storage area devices; magnetic disks, e.g., internal hard disks or removable disks; magneto-optical disks; and CD-ROM and DVD-ROM disks and volatile computer memory, e.g., RAM such as static and dynamic RAM, as well as erasable memory, e.g., flash memory.

Components may be coupled (e.g., communicably coupled) over one or more networks or physically within a device. Coupling may include the capability to transmit data, including instructions, back and forth between the components.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the user device, which acts as a client. Data generated at the user device, e.g., a result of the user interaction, can be received from the user device at the server.

In addition, the logic flows depicted in the figures do not require the particular order shown, or sequential order, to achieve desirable results. In addition, other actions may be provided, or actions may be eliminated, from the described flows, and other components may be added to, or removed from, the described systems. Likewise, actions depicted in the figures may be performed by different entities or consolidated. Furthermore, various separate elements may be combined into one or more individual elements to perform the functions described herein.

While visual and audio signals are mainly described in this invention, other data collection techniques may be employed, such as thermal cues or other wavelength analysis of the face or other portions of the body of the user. These alternative data collection techniques may, for example, reveal underlying emotion/response of the patient, such as changes in blood flow, etc. Additionally, visual depth signal measurements may allow for capture subtle facial surface movement correlated with the symptom that may be difficult to detect with typical color images.

Other implementations not specifically described herein are also within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

It should be noted that any of the above-noted inventions may be provided in combination or individually. Elements of different embodiments described herein may be combined to form other embodiments not specifically set forth above. Elements may be left out of the processes, computer programs, etc. described herein without adversely affecting their operation. Furthermore, the system may be employed in mobile devices, computing devices, cloud based storage and processing. Camera images may be acquired by an associated camera, or an independent camera situated at a remote location. Processing may be similarly be provided locally on a mobile device, or a remotely at a cloud-based location, or other remote location. Additionally, such processing and storage locations may be situated at a similar location, or at remote locations.

While operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

What is claimed is:

1. A computer-implemented method comprising:
    during a session with a subject, presenting a first stimulus to the subject;
    obtaining subject response data comprising audio data or audio-video data of the subject's response to the first stimulus, over a defined time period;
    generating a first subject descriptor data object and a second subject descriptor data object based on the subject response data,
        wherein the first subject descriptor data object comprises a first series of values based on a first segmentation of the defined time period, wherein the second subject descriptor data object comprises a second series of values based on a second segmentation of the defined time period, wherein the second segmentation is different from the first segmentation, and wherein the first series of values and the second series of values characterize action of the subject in response to the first stimulus;

deriving, from the first subject descriptor data object and the second subject descriptor data object, a plurality of biomarkers characterizing a behavior of the subject in response to the first stimulus, wherein values of the plurality of biomarkers are indicative of a severity of a disease in the subject;

based on the values of the plurality of biomarkers, identifying a presence of the disease in the subject;

in response to the identification of the presence of the disease in the subject, selecting an additional stimulus for presentation to the subject, the additional stimulus tailored to induce a response indicative of the severity of the disease;

presenting the additional stimulus to the subject during the session;

determining a value of an additional biomarker based on a response to the additional stimulus; and training a machine learning model using, as inputs of the training,
the values of the plurality of biomarkers and the value of the additional biomarker, and
data characterizing a disease status of the subject, wherein the trained machine learning model is configured to output disease severity levels based on biomarker data;

providing, as input to the trained machine learning model, biomarkers characterizing a response of a second subject to at least one stimulus provided to the second subject; and executing the trained machine learning model to obtain, as output of the trained machine learning model, a disease severity level for the second subject as a function of the biomarkers provided as input to the trained machine learning model.

2. The computer-implemented method of claim 1, comprising:
obtaining a selection by the subject of a presented answer choice in response to a directed question,
wherein the disease severity level is based on the plurality of biomarkers, the value of the additional biomarker, and the selection.

3. The computer-implemented method of claim 1, comprising:
based on the first subject descriptor data object and the second subject descriptor data object, identifying an untruthful response in the response.

4. The computer-implemented method of claim 1, wherein the response to the additional stimulus is associated with multiple biomarkers derivable from the response, and wherein the method comprises:
based on the identification of the presence of the disease in the subject, selecting the additional biomarker from among the multiple biomarkers as a biomarker that is relevant to the disease; and
determining the value of the additional biomarker without determining values of other biomarkers of the multiple biomarkers.

5. The computer-implemented method of claim 1, wherein the first stimulus is a positively valenced question, and wherein the additional stimulus is a negatively valenced question.

6. The computer-implemented method of claim 1, wherein the first stimulus and the additional stimulus are two different types selected from the following stimulus types: a request to make a face having a specified emotion, a request to make a specified sound, and an open-ended question.

7. The computer-implemented method of claim 1, wherein the first subject descriptor data object characterizes facial movement of the subject, wherein the subject response data comprises the audio-video data, and
wherein generating the first subject descriptor data object comprises:
for each frame of the audio-video data, generating an initial data object comprising an indication of (i) whether an action unit is present and (ii) an expressivity of the action unit; and
combining the initial data objects corresponding to each frame, to obtain the first subject descriptor data object.

8. The computer-implemented method of claim 1, wherein the first subject descriptor data object characterizes verbal acoustic characteristics of the response, and
wherein the second subject descriptor data object characterizes speech content of words of the response.

9. The computer-implemented method of claim 8, wherein generating the second subject descriptor data object comprises:
extracting transcribed speech from the subject response data, the transcribed speech comprising transcribed words; and
segmenting the defined time period based on the transcribed words.

10. The method of claim 1, wherein generating the first subject descriptor data object comprises decomposing audio in the audio data or the audio-video data into constituent frequencies.

11. The computer-implemented method of claim 1, wherein the subject response data comprises the audio-video data, wherein the audio-video data includes facial movements of the subject,
wherein the first subject descriptor data object comprises a first time series indicating emotional responses of the subject based on the facial movements,
wherein the second subject descriptor data object comprises a second time series indicating facial tremor of the subject based on the facial movements, and
wherein deriving the plurality of biomarkers comprises:
deriving a first biomarker based on the first time series, and
deriving a second biomarker based on the second time series.

12. The computer-implemented method of claim 1, wherein the plurality of biomarkers comprise biomarkers of two different types selected from the following biomarker types: facial behavior, verbal, and speech.

13. The computer-implemented method of claim 1, wherein generating the first subject descriptor data object comprises applying a machine learning process to the subject response data.

14. The computer-implemented method of claim 1,
wherein the first segmentation comprises a segmentation based on equal-sized sets of a first number of frames of the audio data or the audio-video data, and
wherein the second segmentation comprises a segmentation based on equal-sized sets of a second number of frames of the audio data or the audio-video data, the first number different from the second number.

15. The computer-implemented method of claim 1, comprising:
sending, to a controller controlling a display unit, instructions to present the additional stimulus to the subject using the display unit.

16. The computer-implemented method of claim 1, wherein the first stimulus comprises an instruction to the subject to take a medication, and
wherein the subject response data comprises video data showing the subject taking the medication.

17. The computer-implemented method of claim 1, wherein the first stimulus is presented to the subject by a display of a device,
wherein a processor of the device controls the display, and wherein a camera of the device records the subject response data.

18. The computer-implemented method of claim 1, comprising:
receiving stimulus data, the stimulus data comprising
respective types of a plurality of stimuli presented to the subject, and
time portions corresponding to subject response corresponding to each of the plurality of stimuli; and
deriving the plurality of biomarkers based on the respective types of the plurality of stimuli.

19. The computer-implemented method of claim 1,
wherein the first segmentation comprises a segmentation based on equal-sized sets of one or more frames of the audio data or the audio-video data, and
wherein the second segmentation comprises a segmentation based on words or phrases of the response.

20. A system comprising:
a display;
a controller, the controller configured to send instructions to the display to present a first stimulus to a subject during a session;
a sensor configured to record subject response data comprising audio data or audio-video data of the subject's response to the first stimulus over a defined time period; and
a computer, the computer configured to perform operations comprising:
obtaining the subject response data,
generating a first subject descriptor data object and a second subject descriptor data object based on the subject response data,
wherein the first subject descriptor data object comprises a first series of values based on a first segmentation of the defined time period,
wherein the second subject descriptor data object comprises a second series of values based on a second segmentation of the defined time period, wherein the second segmentation is different from the first segmentation, and
wherein the first series of values and the second series of values characterize action of the subject in response to the first stimulus;
deriving, from the first subject descriptor data object and the second subject descriptor data object, a plurality of biomarkers characterizing a behavior of the subject in response to the first stimulus, wherein values of the plurality of biomarkers are indicative of a severity of a disease in the subject;
based on the values of the plurality of biomarkers, identifying a presence of the disease in the subject;

in response to the identification of the presence of the disease in the subject, selecting an additional stimulus for presentation to the subject, the additional stimulus tailored to induce a response indicative of the severity of the disease;
presenting the additional stimulus to the subject during the session;
determining a value of an additional biomarker based on a response to the additional stimulus; and
training a machine learning model using, as inputs of the training,
the values of the plurality of biomarkers and the value of the additional biomarker, and
data characterizing a disease status of the subject,
wherein the trained machine learning model is configured to output disease severity levels based on biomarker data;
providing, as input to the trained machine learning model, biomarkers characterizing a response of a second subject to at least one stimulus provided to the second subject; and
executing the trained machine learning model to obtain, as output of the trained machine learning model, a disease severity level for the second subject as a function of the biomarkers provided as input to the trained machine learning model.

21. The system of claim 20, wherein the operations comprise:
sending an instruction to the controller to have the display present the additional stimulus to the subject.

22. The system of claim 20, wherein the display, the controller, and the sensor are integrated into a portable device.

23. The system of claim 20, wherein the operations comprise:
obtaining a selection by the subject of a presented answer choice in response to a directed question,
wherein the disease severity level is based on the plurality of biomarkers, the value of the additional biomarker, and the selection.

24. The system of claim 20, wherein generating the second subject descriptor data object comprises:
extracting transcribed speech from the subject response data, the transcribed speech comprising transcribed words; and
segmenting the defined time period based on the transcribed words, so that the second subject descriptor data object characterizes speech content of words of the response.

25. The system of claim 20, wherein the first stimulus and the additional stimulus are two different types selected from the following stimulus types: a request to make a face having a specified emotion, a request to make a specified sound, and an open-ended question.

26. The system of claim 20, wherein the operations comprise:
receiving, from the controller, stimulus data, the stimulus data comprising
respective types of a plurality of stimuli presented to the subject, and
time portions corresponding to subject response corresponding to each of the plurality of stimuli; and
deriving the plurality of biomarkers based on the respective types of the plurality of stimuli.

* * * * *